(12) United States Patent
Conn

(10) Patent No.: US 10,335,193 B2
(45) Date of Patent: Jul. 2, 2019

(54) RETROGRADE ENTRY ANTEGRADE PLACEMENT FOR FEMORAL ARTERY ACCESS

(71) Applicant: John Miller Conn, Colorado Springs, CO (US)

(72) Inventor: John Miller Conn, Colorado Springs, CO (US)

(73) Assignee: POLR ANGIOSCIENCE, LLC, Colorado Springs, CO (US)

( * ) Notice: Subject to any disclaimer, the term of this patent is extended or adjusted under 35 U.S.C. 154(b) by 434 days.

(21) Appl. No.: 15/256,559

(22) Filed: Sep. 3, 2016

(65) Prior Publication Data

US 2017/0007292 A1    Jan. 12, 2017

Related U.S. Application Data

(60) Continuation-in-part of application No. 14/593,923, filed on Jan. 9, 2015, now abandoned, which is a
(Continued)

(51) Int. Cl.
*A61B 17/34* (2006.01)
*A61M 25/09* (2006.01)
(Continued)

(52) U.S. Cl.
CPC ............ *A61B 17/3403* (2013.01); *A61B 6/12* (2013.01); *A61B 8/0841* (2013.01);
(Continued)

(58) Field of Classification Search
CPC .............. A61B 17/34; A61B 17/06109; A61B 2017/061; A61M 25/0026; A61M 25/06; A61M 25/0662; A61M 25/065
See application file for complete search history.

(56) References Cited

U.S. PATENT DOCUMENTS

| 4,027,668 A * | 6/1977 | Dunn ................... A61M 25/02 |
| | | 604/164.01 |
| 4,033,331 A | 7/1977 | Guss et al. |
| (Continued) | | |

OTHER PUBLICATIONS

Official Action for U.S. Appl. No. 13/300,533, dated Mar. 31, 2014, 13 pages.
(Continued)

*Primary Examiner* — Ashley L Fishback
(74) *Attorney, Agent, or Firm* — Stanley J. Gradisar Attorney At Law, LLC; Stanley J. Gradisar

(57) ABSTRACT

A Retrograde Entry Antegrade Placement (REAP™) method and apparatus facilitate the antegrade (i.e., in the direction of blood flow) placement of endovascular devices for treatment of lower extremity arterial disease. Initially, a retrograde entry is made into the arterial system of a patient at an entry point with a curved needle, which then exits at an exit point proximal to the entry point, with a first wire then passed through the lumen of the curved needle. From the skin exit point, a Dual-Lumen Access Director (DAD) device is advanced in the antegrade direction down the first wire in a first lumen and enters the CFA 1 lumen. A second wire is passed down a second lumen in the DAD device and follows the SFA lumen in the antegrade direction. The DAD device is removed, and a standard dilator and sheath is inserted over the second wire and the endovascular treatment begins.

20 Claims, 36 Drawing Sheets

Related U.S. Application Data division of application No. 13/300,533, filed on Nov. 18, 2011, now Pat. No. 8,961,549.

(60) Provisional application No. 61/444,928, filed on Feb. 21, 2011, provisional application No. 61/415,188, filed on Nov. 18, 2010.

(51) Int. Cl.

| | |
|---|---|
| *A61B 17/00* | (2006.01) |
| *A61B 6/12* | (2006.01) |
| *A61M 29/02* | (2006.01) |
| *A61B 8/08* | (2006.01) |
| *A61B 17/02* | (2006.01) |
| *A61B 17/06* | (2006.01) |
| *A61M 25/06* | (2006.01) |
| *A61B 6/00* | (2006.01) |
| *A61M 39/02* | (2006.01) |
| *A61B 17/22* | (2006.01) |
| *A61B 17/221* | (2006.01) |

(52) U.S. Cl.
CPC .... *A61B 17/0218* (2013.01); *A61B 17/06109* (2013.01); *A61B 17/3415* (2013.01); *A61B 17/3423* (2013.01); *A61B 17/3478* (2013.01); *A61M 25/065* (2013.01); *A61M 25/09* (2013.01); *A61M 29/02* (2013.01); *A61B 6/485* (2013.01); *A61B 6/504* (2013.01); *A61B 2017/00778* (2013.01); *A61B 2017/2217* (2013.01); *A61B 2017/22038* (2013.01); *A61B 2017/3405* (2013.01); *A61B 2017/3413* (2013.01); *A61B 2017/3425* (2013.01); *A61B 2017/3454* (2013.01); *A61M 39/02* (2013.01); *A61M 2039/0258* (2013.01); *A61M 2039/0276* (2013.01); *A61M 2210/12* (2013.01)

(56) References Cited

U.S. PATENT DOCUMENTS

| | | | |
|---|---|---|---|
| 4,769,005 | A | 9/1988 | Ginsburg et al. |
| 5,149,330 | A | 9/1992 | Brightbill |
| 5,195,962 | A | 3/1993 | Martin et al. |
| 6,371,935 | B1 | 4/2002 | Macoviak et al. |
| 8,961,549 | B2 | 2/2015 | Conn |
| 9,265,916 | B2 | 2/2016 | Conn |
| 9,468,742 | B2 | 10/2016 | Conn |
| 2004/0220473 | A1 | 11/2004 | Lualdi |
| 2013/0072900 | A1 | 3/2013 | Colantonio |
| 2015/0126936 | A1 | 5/2015 | Conn |
| 2015/0165164 | A1 | 6/2015 | Conn |

OTHER PUBLICATIONS

Notice of Allowance for U.S. Appl. No. 13/300,533, dated Oct. 10, 2014, 7 pages.
Official Action for U.S. Appl. No. 14/593,923, dated Mar. 10, 2015, 11 pages.
Official Action for U.S. Appl. No. 14/593,980, dated Mar. 12, 2015, 12 pages.
Official Action for U.S. Appl. No. 14/593,923, dated Oct. 8, 2015, 10 pages.
Notice of Allowance for U.S. Appl. No. 14/593,980, dated Oct. 13, 2015, 9 pages.
$2^{nd}$ Notice of Allowance for U.S. Appl. No. 14/593,980, dated Dec. 8, 2015, 3 pages.
Official Action for U.S. Appl. No. 14/593,921, dated Dec. 24, 2015, 10 pages.
Official Action for U.S. Appl. No. 14/593,921, dated Apr. 22, 2016, 8 pages.
Official Action for U.S. Appl. No. 14/593,923, dated May 3, 2016, 5 pages.
Notice of Allowance for U.S. Appl. No. 14/593,921, dated Sep. 6, 2016, 6 pages.

\* cited by examiner

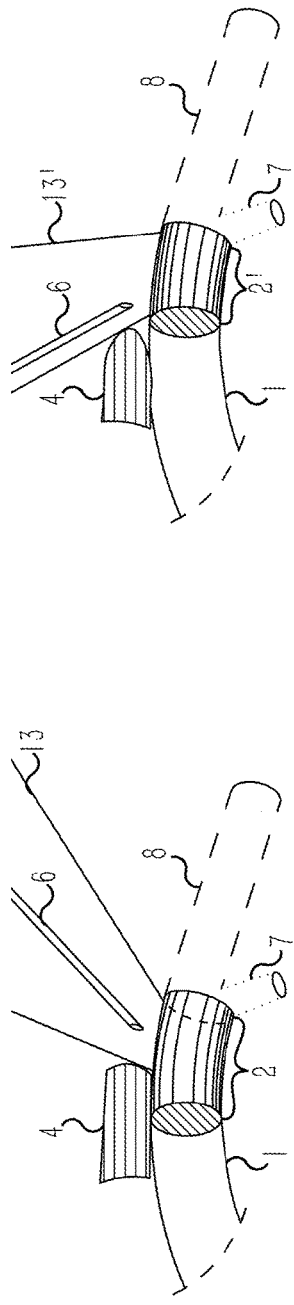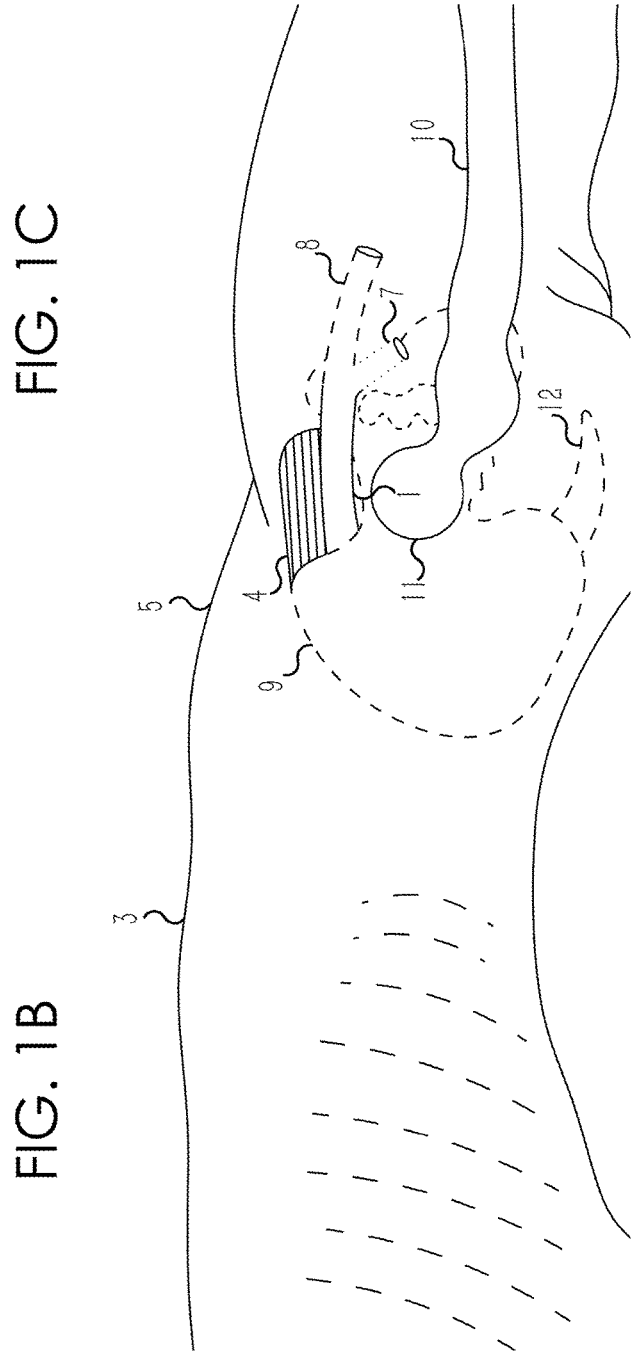

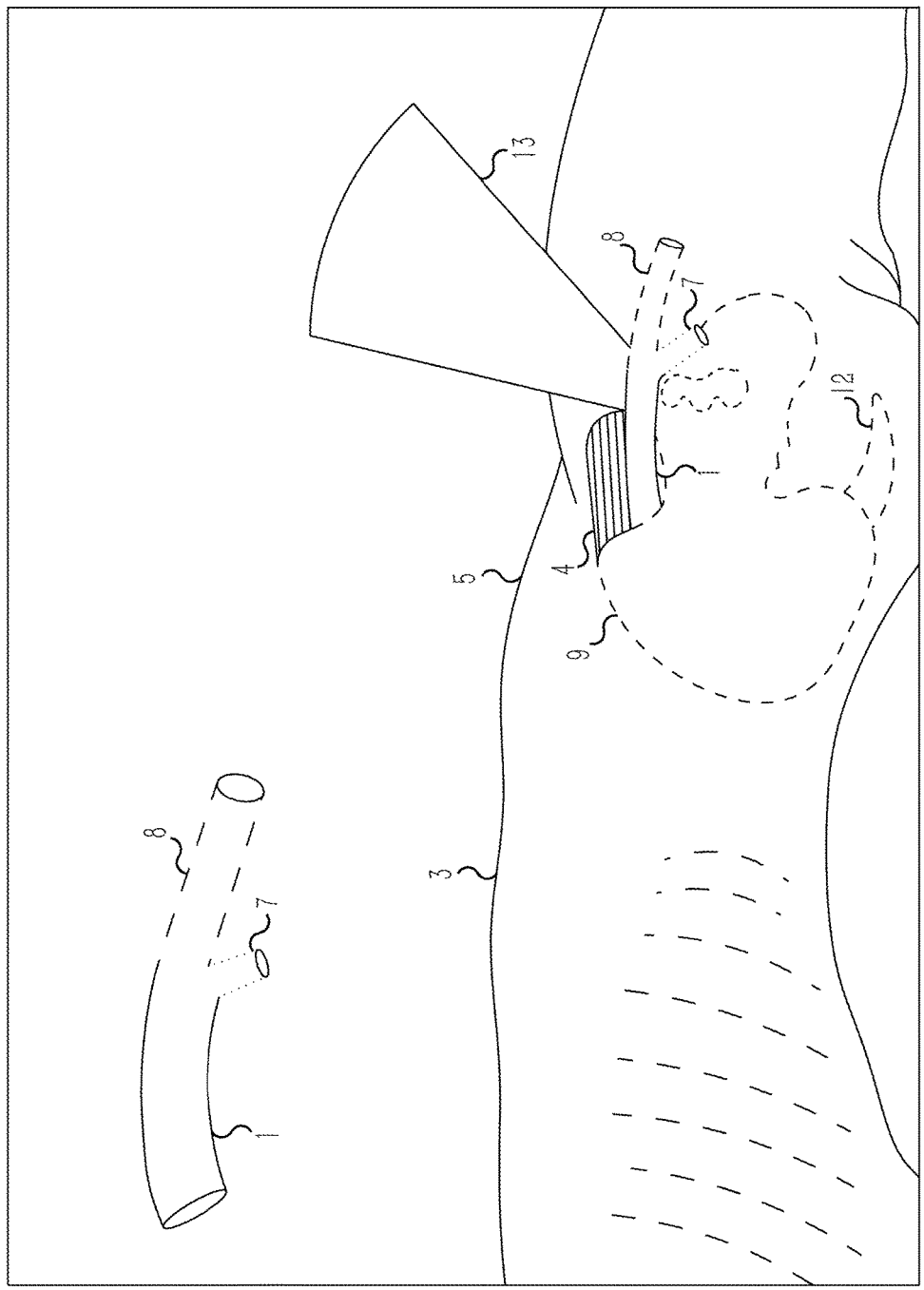

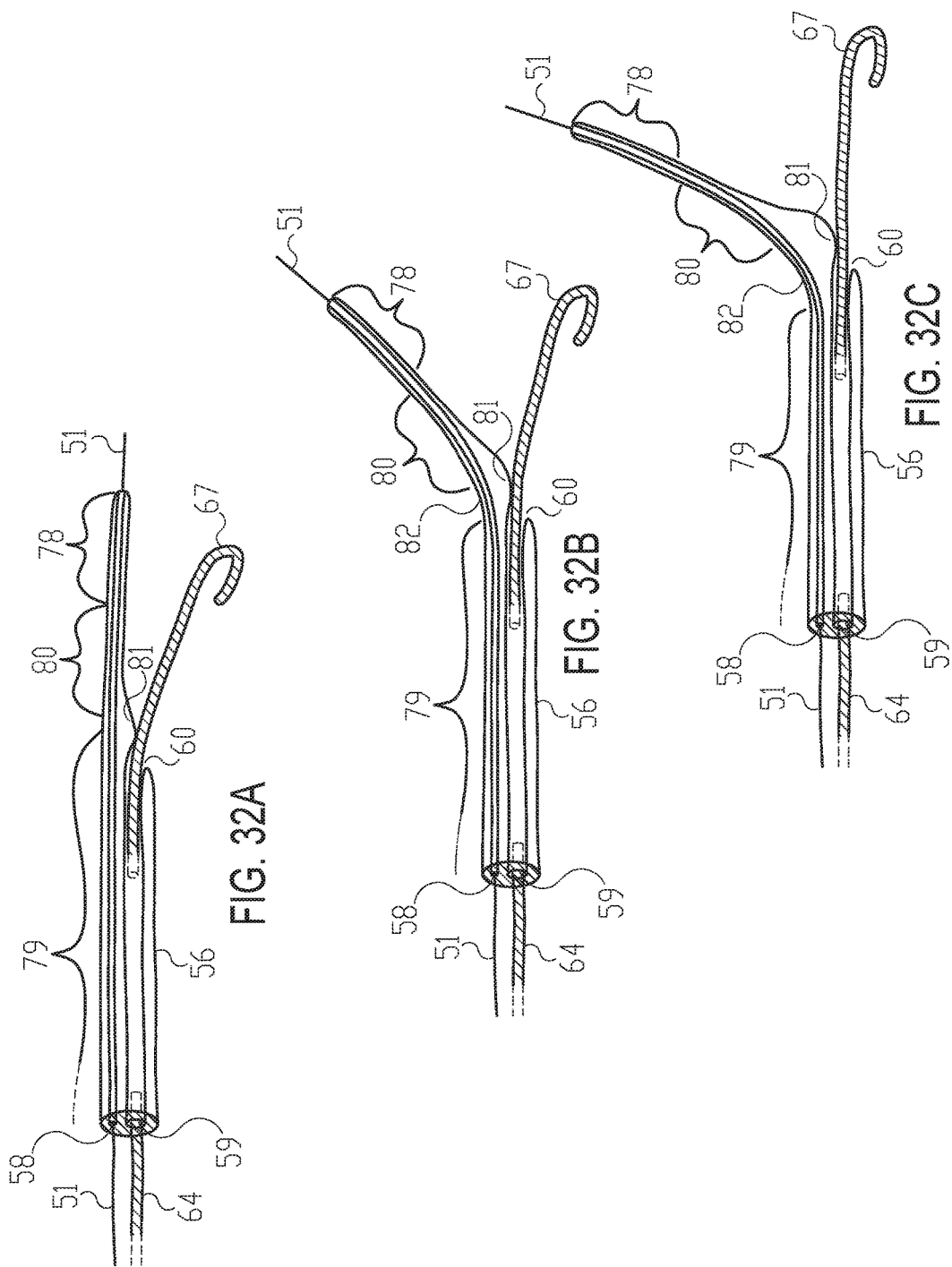

RETROGRADE ENTRY ANTEGRADE PLACEMENT FOR FEMORAL ARTERY ACCESS

CROSS-REFERENCES TO RELATED APPLICATIONS

This application is a continuation-in-part application of application Ser. No. 14/593,923 filed on Jan. 9, 2015 titled "Retrograde Access Antegrade Placement For Femoral Artery Access" which is incorporated herein by reference in its entirety for all that is taught and disclosed therein, and is a division of U.S. patent application Ser. No. 13/300,533 Titled "Retrograde Entry Antegrade Placement For Femoral Artery Access" Filed On Nov. 18, 2011, now U.S. Pat. No. 8,961,549 which issued on Feb. 24, 2015, which claims the benefit of U.S. Provisional Application Ser. No. 61/415,188 filed on Nov. 18, 2010 titled "Retrograde Access Antegrade Placement For Femoral Artery Access" and U.S. Provisional Application Ser. No. 61/444,928 filed on Feb. 21, 2011 titled "Retrograde Entry Antegrade Placement For Femoral Artery Access," both of which are incorporated herein by reference in their entirety for all that is taught and disclosed therein. This application is also related to application Ser. No. 14/593,980 titled "Retrograde Access Antegrade Placement For Femoral Artery Access" filed on Jan. 9, 2015, now U.S. Pat. No. 9,265,916 which issued on Feb. 23, 2016 which is incorporated herein by reference in its entirety for all that is taught and disclosed therein.

BACKGROUND

1. Rationale for Choice of the Femoral Artery in Vascular Access

The common femoral artery is the primary entry site for interventional vascular access. The majority of procedures involving interventions upon major arteries, including those of the limbs, neck, viscera, heart and head, are performed through needle entry into the common femoral artery. In the vast majority of cases, certainly greater than 95% in the USA, needle entry into the common femoral artery is done via a retrograde stick (i.e., a needle enters the artery in a direction opposite the flow of blood).

Antegrade stick (i.e., a needle enters the artery in the same direction as the flow of blood), in which the operator stands on the patient's left facing the feet, is rarely employed. There are several reasons for the facts stated above.

The first reason is operator-based. The stance and posture of a retrograde approach to the common femoral artery are quite natural. Most persons (85-92%) are right-hand dominant. An operator standing at the supine patient's right groin and facing towards the patient's head will find an ideal ergonomic position for right hand maneuvers involving reach, grasp, pinch, push-pull, pronation and supination of the hand and wrist. The operator's natural range of motion of the combined finger, wrist, and elbow joints very comfortably blankets a work area centered upon the groin.

The second reason is target size. The common femoral artery (CFA) lumen diameter has been extensively studied in health and disease states, and in a patient population typically provides a minimum lumen diameter of 4 mm to 6 mm. In many patients the lumen diameter reaches 8 to 10 mm. Catheter bores for common vascular interventions typically range from 6 French (diameter 2 mm) to 8 French (diameter 2.7 mm). The CFA thus easily accommodates the outside diameters of tubular instrumentation.

Length of the target vessel is also important, as the approach angle of the needle determines potential tip placement at each depth. In 200 angiographic measurements the mean common femoral artery length was 43.3 mm, and it was given as 22.5 to 50 mm in 75% of a large number of direct measurements.

The above explains why the CFA is frequently chosen as a target. It must be explained, however, why the retrograde rather than the antegrade stick route is the predominant choice. FIGS. 1A, 1B, and 1C show the target segment of the Common Femoral Artery (CFA). An internal view of Body 3 is shown in FIG. 1A depicting CFA 1 (shown in solid lines), Inguinal Ligament 4, Profunda Femoris Artery (PFA) 7 (shown in dotted lines), Superficial Femoral Artery (SFA) 8 (shown in dashed lines), Anterior Superior Iliac Spine (ASIS) 9, Right Femur 10, Femoral Head 11, and Coccyx 12. One reason the retrograde rather than the antegrade stick route is the predominant choice is the longer Target Segment 2 length of CFA 1 when Needle 6 approaches retrograde (FIG. 1B) rather than Target Segment 2' of CFA 1 when Needle 6 approaches antegrade (FIG. 1C). This is due to the multiple topographic curvatures of Body 3 as well as obstruction by the Inguinal Ligament 4 and the Abdominal Protuberance 5. Additionally, both the topographic window for needle entry into the skin, and the Swath 13, 13' (the conical three-dimensional zone through which Needle 6 may pass in order that its tip will strike Target Segment 2, 2') are also smaller in the antegrade stick approach (FIG. 1C) to CFA 1 as compared with the traditional retrograde pathway (FIG. 1B).

Body habitus is frequently abnormal in patients undergoing treatment for vascular disease. In the retrograde stick approach to CFA 1, operators have long been comforted in their use of a traditional retrograde needle placement by the fact that the approach angle and swath of the needle pathway are not materially altered by patient bulk (see FIG. 2A with normal Body 3 and Abdominal Protuberance 5 and FIG. 2B with abnormal Body 3' and Abdominal Protuberance 5'). Longer needles may be needed to traverse the thicker body wall, but the approach angle and Swath 13 for access need not change.

In the antegrade stick technique, however, body habitus substantially narrows Swath 13' of potential needle passage (see FIGS. 3A and 3B). Because CFA 1 Target Segment 2' is also reduced in length, the technical challenges in the antegrade approach to a large patient are often insurmountable.

The ideal approach angle for a needle entering CFA 1 is between 30 and 45 degrees. If much steeper, 60 to 90 degrees, the subsequent placement of larger bore devices will lead to crimping or, worse, laceration ("cheese-wire" effect) of the arterial wall, with hemorrhage. In almost no cases of antegrade approach to CFA 1 is the ideal angle not blocked by Inguinal Ligament 4 and other structures superior to the groin (see FIG. 1).

A third technical hindrance to catheterization of SFA 8 via an antegrade directed needle stick is the problem of the Wire-Extrusion Vector 14 (see FIG. 4A). Operators have long experienced the ease with which the retrograde stick approach places a wire almost unfailingly in the iliac system. This is because of the unique spacial positioning of the needle tip aimed retrograde. Because of the natural approach angle which matches with the direction of CFA 1 as it passes under Inguinal Ligament 4 and becomes the posterior-directed External Iliac Artery (EIA) 38 (see FIG. 9), extrusion of the wire from Needle Bore 15 is virtually always aimed in the right direction.

In the case of an antegrade directed needle stick, the opposite is true. The mandatory vertical and posterior aim of Needle Bore 15 and Wire-Extrusion Vector 14' almost always ensures that the wire will be extruded in the direction of PFA 7, instead of entering the SFA 8. Because Swath 13' for Needle 6 approach is so narrow in the antegrade technique, the needle tip itself can move through only a very small swing angle as the operator attempts to correct its aim, misdirecting the wire into the PFA 7 (see FIGS. 4B and 4C).

The fourth reason is control and closure of the arteriotomy. Intentional entry into SFA 8 for placement of larger (5 French or greater) devices, is problematic. At the origin of SFA 8 from CFA 1 the diameter of the artery drops precipitously to a lumen diameter of less than 5 mm, as flow divides from CFA 1 into two substantial branch channels, SFA 8 and PFA 7. SFA 8 is not only smaller in diameter but possesses decreased arterial wall strength and integrity in comparison to CFA 1. Surgeons will often find the SFA 8 wall friable and unforgiving when it is sutured, a problem compounded by the artery's smaller lumen. SFA 8 is therefore avoided whenever possible as a site in which to originate a bypass graft, with CFA 1's stronger and larger structure being preferred. FIG. 5A shows an 8 French (diameter 2.7 mm) Sheath 16 entering into a CFA 1 having a Lumen 17 of 6 mm in diameter and a Wall Thickness 18 of 2 mm. Also shown for comparison is 8 French Sheath 16 entering into a SFA 8 having a Lumen 19 of 4 mm in diameter and a Wall Thickness 20 of 1.5 mm.

The catheter interventionalist placing a sheath in an artery faces an additional problem. The tubular mass inserted creates a roughly circular arteriotomy corresponding to the outside diameter of that sheath. This arteriotomy must then be closed in some way, i.e., sealed, once the sheath is removed. 8 French Sheath 16 inserted into CFA 1 produces an arteriotomy which occupies much less of a percentage circumference of the vessel than in SFA 8 (see FIG. 5B). Compared to CFA 1, an 8 French arteriotomy in SFA 8 produces a much larger break in the circular integrity of SFA 8, allowing Lumen 19 to gape when 8 French Sheath 16 is removed. Given two tubes, one larger and one smaller, a slit of the same length made transversely in each will disrupt shape-retention properties and tubular integrity much more in the smaller than in the larger tube. For this reason, SFA 8 more frequently demonstrates bleeding or disruption when entered with large bore devices.

Studies have shown as much as a 10% rate of pseudoaneurysm formation when sizeable catheters are deliberately placed into SFA 8. This is likely due in part to the difficulty in compressing SFA 8 manually after sheath removal. CFA 1 can be compressed by fingertip pressure on the skin overlying the puncture site, because the round bony surface of the Femoral Head 11 lies immediately beneath (see FIG. 1). SFA 8 has no corresponding bone structure deep to it which would allow effective manual compression. In the final analysis, the safest and most certain pathway for a large-bore catheter into the vascular tree is via an arteriotomy in the CFA 1.

2. Anatomy of the Femoral Artery

Anatomy of the femoral zone is complex and can be deceiving to the unschooled. CFA 1 lies in a depression, Femoral Triangle 21, seen immediately below the fold of the groin (see FIG. 6). Emerging from beneath Inguinal Ligament 4 as it leaves the pelvic cavity, CFA 1 (not visible in FIG. 6) enters the thigh at a point equidistant from ASIS 9 and the pubic symphysis (not shown in FIG. 6). CFA 1 is a continuation of a large artery—the EIA 38 (see FIG. 9). The vessel simply changes names to become CFA 1 as it crosses beneath Inguinal Ligament 4.

In the upper thigh, CFA 1 resides between the Femoral Vein 22 medially and the femoral nerve laterally (not shown in FIG. 6), in a triangular space with distinct boundaries. Superiorly is Inguinal Ligament 4; laterally, Sartorius Muscle 23; and medially, Adductor Longus Muscle 24. Deep to the femoral artery, separating it from the spherical Femoral Head 11, is the psoas major tendon (not shown in FIG. 6). Superficial to the femoral artery, forming a roof over Femoral Triangle 21 in the upper thigh is the Fascia Lata 25.

3. Topography of Femoral Artery Access

Body-surface planes and curvatures in the femoral depression tend to prohibit an antegrade approach. The femoral arteries (CFA 1, PFA 7, and SFA 8) reside in the femoral triangle concavity. Access to the femoral branches is affected by the depth of that depression, as well as the other compound curvatures of the abdomen, pelvis, pubis and thighs (see FIG. 7). In smaller and thinner persons, the curvatures are still present but may be less pronounced. But in heavier bulkier individuals the mounding and angulation of tissue can present formidable obstacles.

There are four prominent topographic curvatures shown in FIG. 7. Abdominal Protuberance 5 is the abdominopelvic protuberance, sometimes exaggerated as a pannus, containing the muscular abdominal wall, and fatty tissue, which if large, may also include the anterior peritoneum containing the small intestine and even the colon. Transverse Groove 26 is the furrow or crease formed where the inguinal canal meets the upper thigh. Muscular Curvature 27 is the mound of medial and lateral musculature bounding the depression of the Femoral Triangle 21. Sub-Pubic Pit 28 is the empty space defined by the confluence of the pubis and inner thighs.

4. Known Difficulties of the Antegrade Approach

Antegrade access is not widely touted in the literature, nor utilized extensively, due to its technical difficulty. For the foregoing reasons, medical authors have repeatedly cautioned against the antegrade approach. Dr. Giuseppe Biondi-Zoccai recommends a minimum caseload of 60 antegrade procedures to assure competency. Dr. Schneider noted that even the easier, retrograde approach resulted in less than optimal needle placement in 56% of cases, including 13% entirely beyond the borders of CFA 1. Dr. Schneider advocates against a routine antegrade approach. Dr. Narins emphasizes the steeper learning curve and increased risk of vascular complications with antegrade stick of the common femoral artery.

As a result of these and other problems, operators have not embraced antegrade femoral access. Interventionalists have instead relied upon the safety and practicality of the retrograde up-and-over technique: to reach the right leg, stick the left common femoral artery; for the left leg, stick the right common femoral artery. Nonetheless, there are enormous advantages to be gained from the antegrade approach.

5. Impetus to Develop a Safe and Easy Antegrade Approach to the Femoral Artery

Antegrade placement and manipulation of endovascular treatment devices is the most promising frontier for treatment of lower extremity arterial disease. Manufactured devices for precise work in the lower extremities—particularly if utilized to treat targets below the knee—tend to be difficult to maneuver when working over the distances and past the multiple twisting turns involved in the retrograde up-and-over access technique.

In the up-and-over method a catheter which enters the right common femoral artery retrograde must immediately track deep posteriorly following the external iliac artery down into the pelvis along the sacrum. Then it must rise abruptly within the common iliac artery, turning sharply towards the midline. The catheter then crosses the aortic bifurcation at an angle greater than 270 degrees. Another set of acute angles ensues as the catheter backtracks through the pelvis repeating the iliac course and curvatures in reverse. It will then emerge beneath the inguinal ligament, cross the "speed-bump" of the contralateral common femoral artery and its branches. At this point the catheter must be maneuvered along a steadily narrowing pathway in the superficial femoral artery until it reaches another s-curve, this time in the anterior-posterior plane, as it enters the popliteal artery and traverses the knee. Thereafter lie three successive sharp-angled take-offs of arterial branches whose diameter is now less than 3 mm, less if badly diseased.

To accomplish this, catheters must be longer. However, the increased length sacrifices pushability and control. Tight atherosclerotic plaques must be crossed by pushing in the opposite direction of catheter path at the target. This is not only mechanically disadvantageous, but requires "opposite-think" and 3-dimensional conceptual efforts which are not always easy for an operator. As a result, widespread application of certain devices has been limited by difficulty in controlling the catheters at distant lesions. Because of the predominant pattern of retrograde femoral access, manufacturers have been forced to compromise device control for length, and performance has suffered. Effective therapeutic devices which function optimally in the antegrade direction have thus been hindered in reaching a patient population which could benefit by their use.

There are natural advantages to the right-hand dominant operator which accrue when standing at the patient's right groin facing the head. In antegrade access to the legs these advantages are also in full play. Once antegrade access is established, the operator stands at the supine patient's left hip. So positioned, maneuvers of the operator's hands are directed towards the target vessels, along the axis of the catheter system. This affords all the mechanical and spacial advantages with which operators are familiar with in traditional retrograde access to the upper body.

A solution to these difficulties in access to the leg arteries would be the development of a process which makes antegrade access easy, safe, and routine. The technique should have a short learning curve, and should utilize device configurations with which the operator is already familiar. Ideally it should be performed in the operator position and via the anatomic approach most familiar to practitioners. The procedure and associated devices described below are designed to provide such a solution.

SUMMARY OF THE INVENTION

This Summary is provided to introduce in a simplified form a selection of concepts that are further described below in the Detailed Description. This Summary is not intended to identify key features or essential features of the claimed subject matter, nor is it intended to be used to limit the scope of the claimed subject matter.

A Retrograde Entry Antegrade Placement (REAP™) method and apparatus facilitate the antegrade (i.e., in the direction of blood flow) placement of endovascular devices (i.e., working within the lumen of vascular structures) for treatment of lower extremity arterial disease.

BRIEF DESCRIPTION OF THE DRAWINGS

FIGS. 1A, 1B, and 1C show the target segment of the common femoral artery.

FIG. 2A shows the retrograde-stick approach in a normal body habitus.

FIGS. 32A, 32B, and 32C show the bump configuration at the oval orifice that serves to direct the treatment wire in an axial direction down the vessel when the tip end of the dual-lumen access director is deflected when exiting the SFA.

Figure 2B:
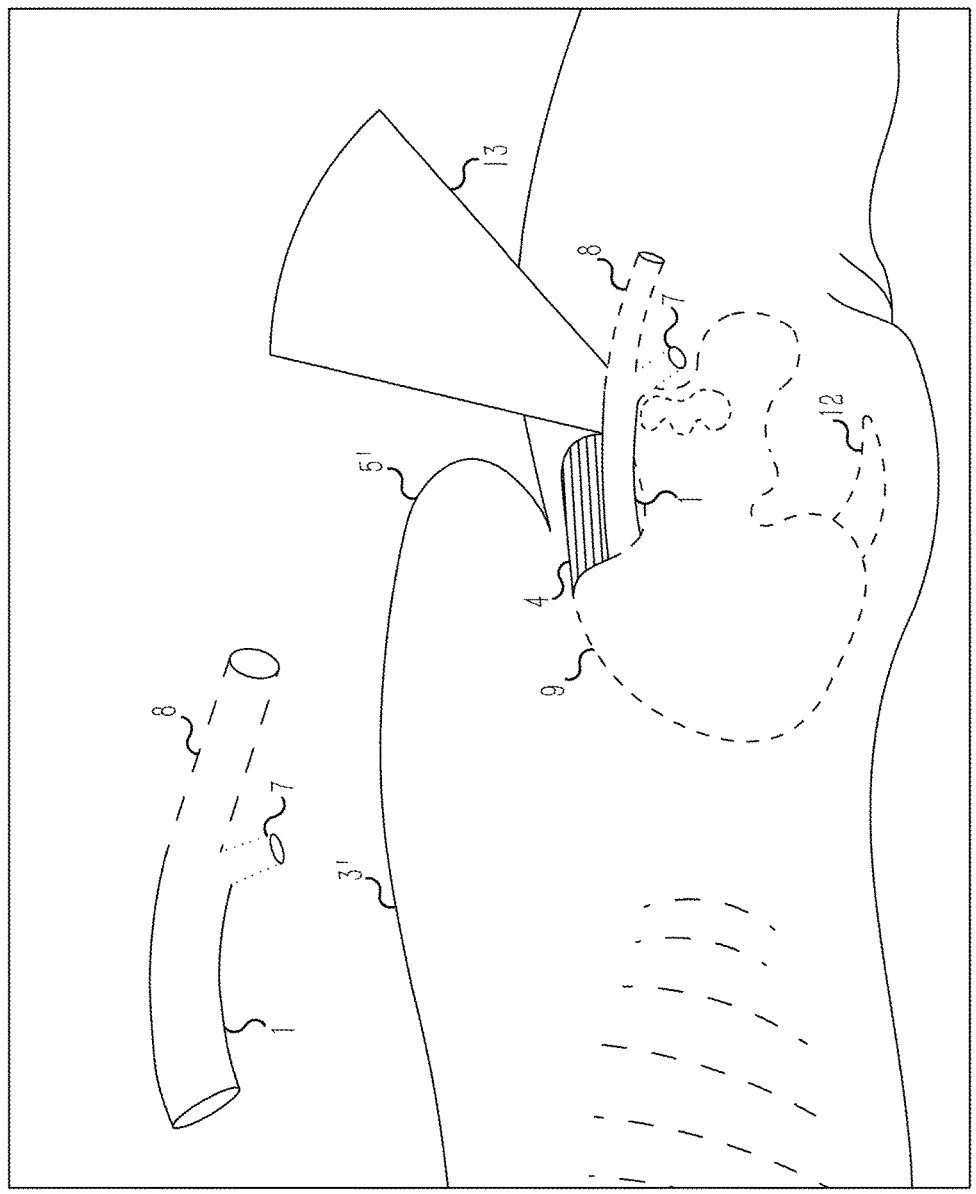
FIG. 2B shows the retrograde-stick approach in a large body habitus.
Figure 3A:
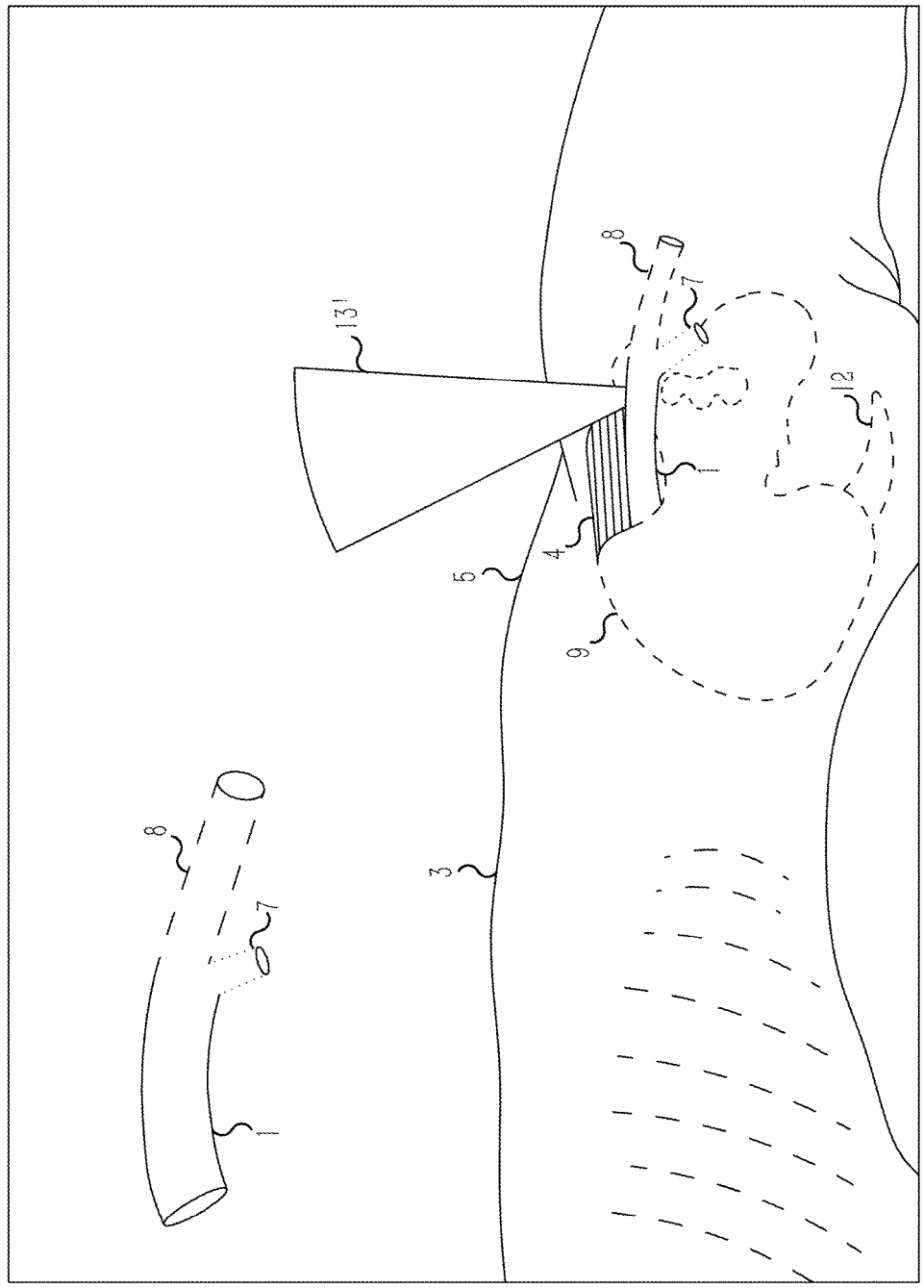
FIG. 3A shows the antegrade-stick approach in a normal body habitus.
Figure 3B:
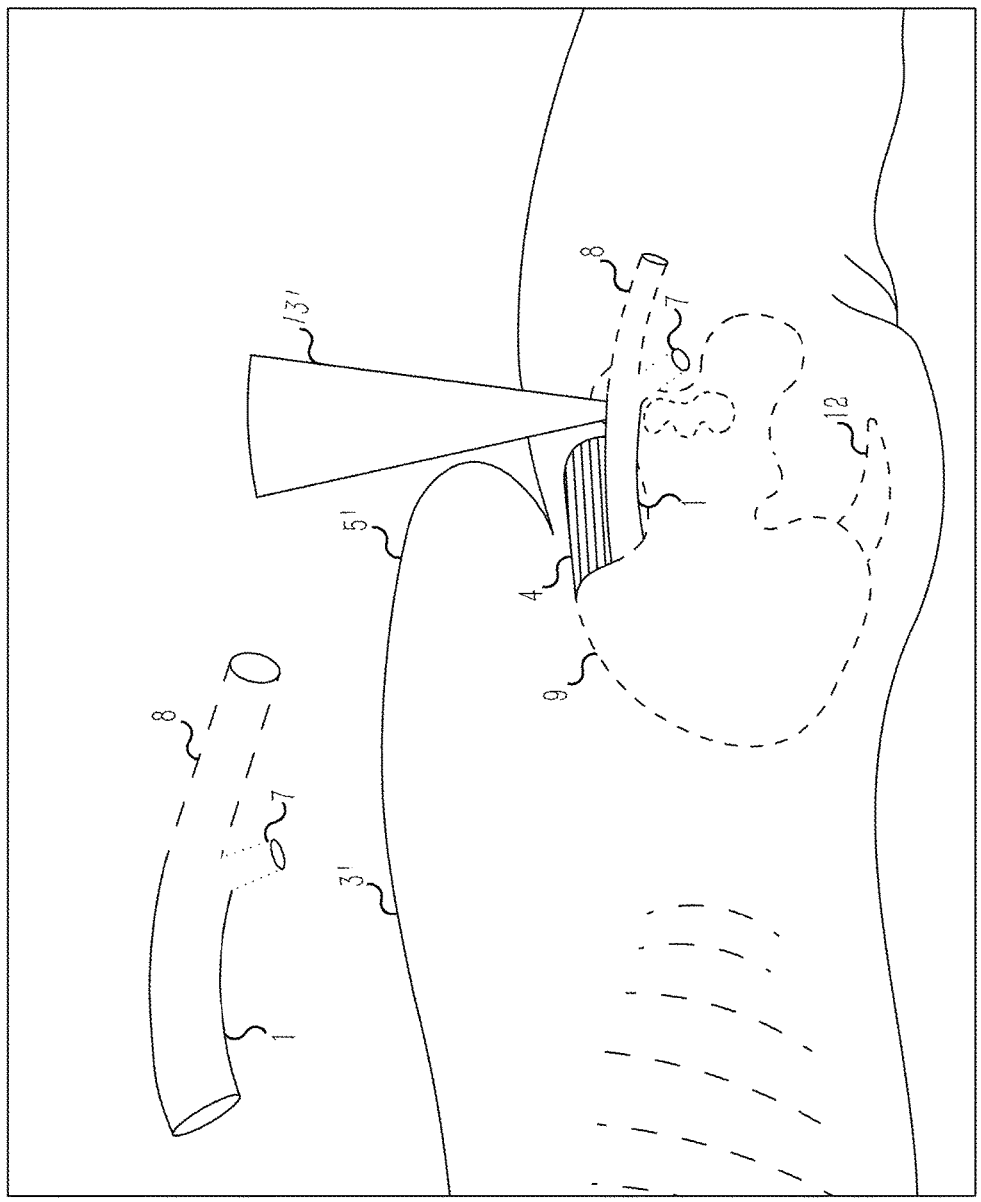
FIG. 3B shows the antegrade-stick approach in a large body habitus.
Figure 4A:
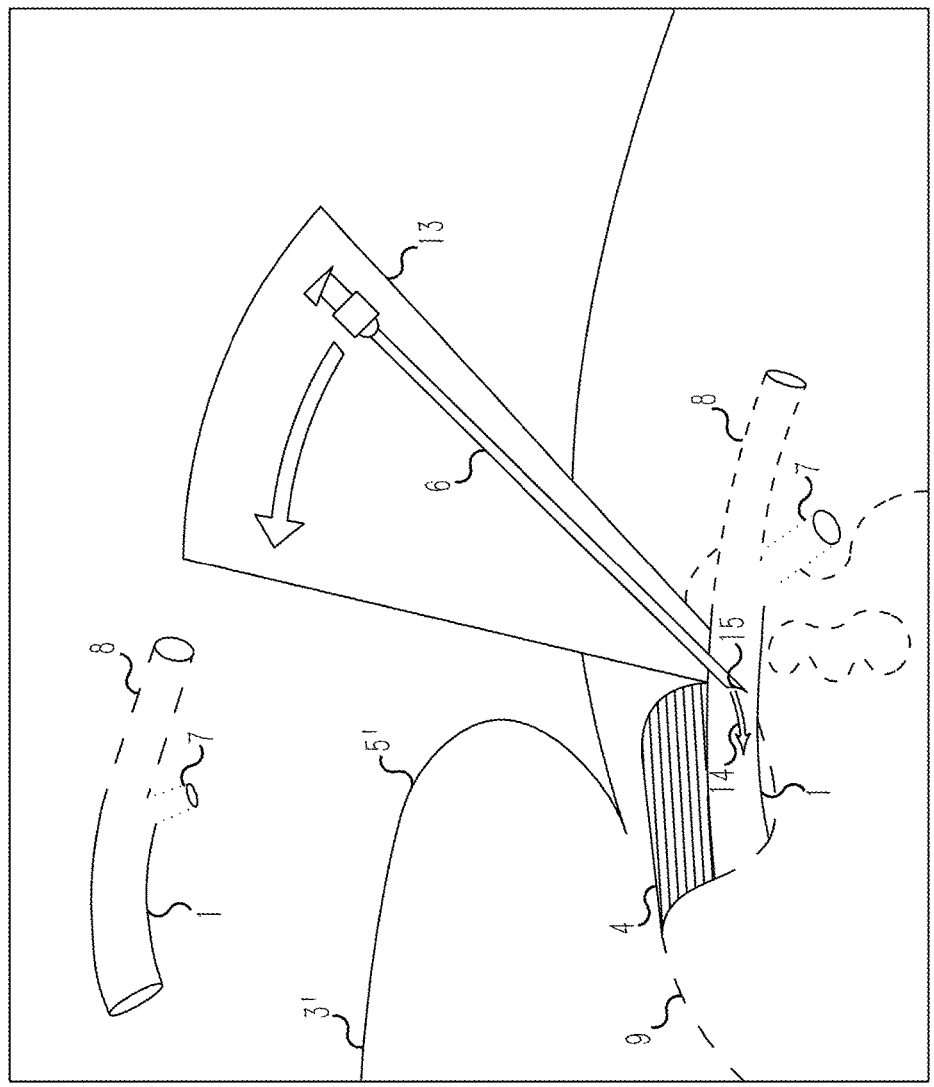
FIG. 4A shows the wire extrusion vector in the retrograde-stick approach.
Figure 4B:
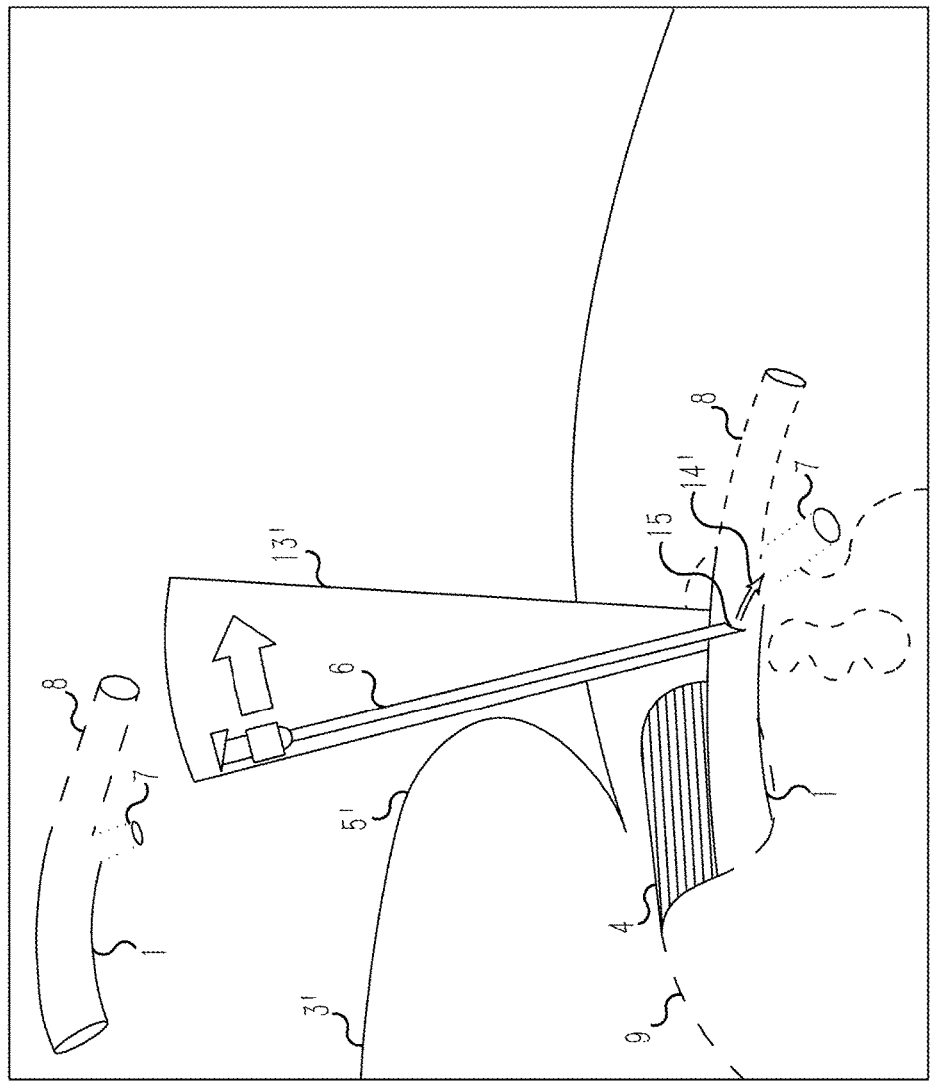
FIG. 4B shows the wire extrusion vector in the antegrade-stick approach.
Figure 4C:
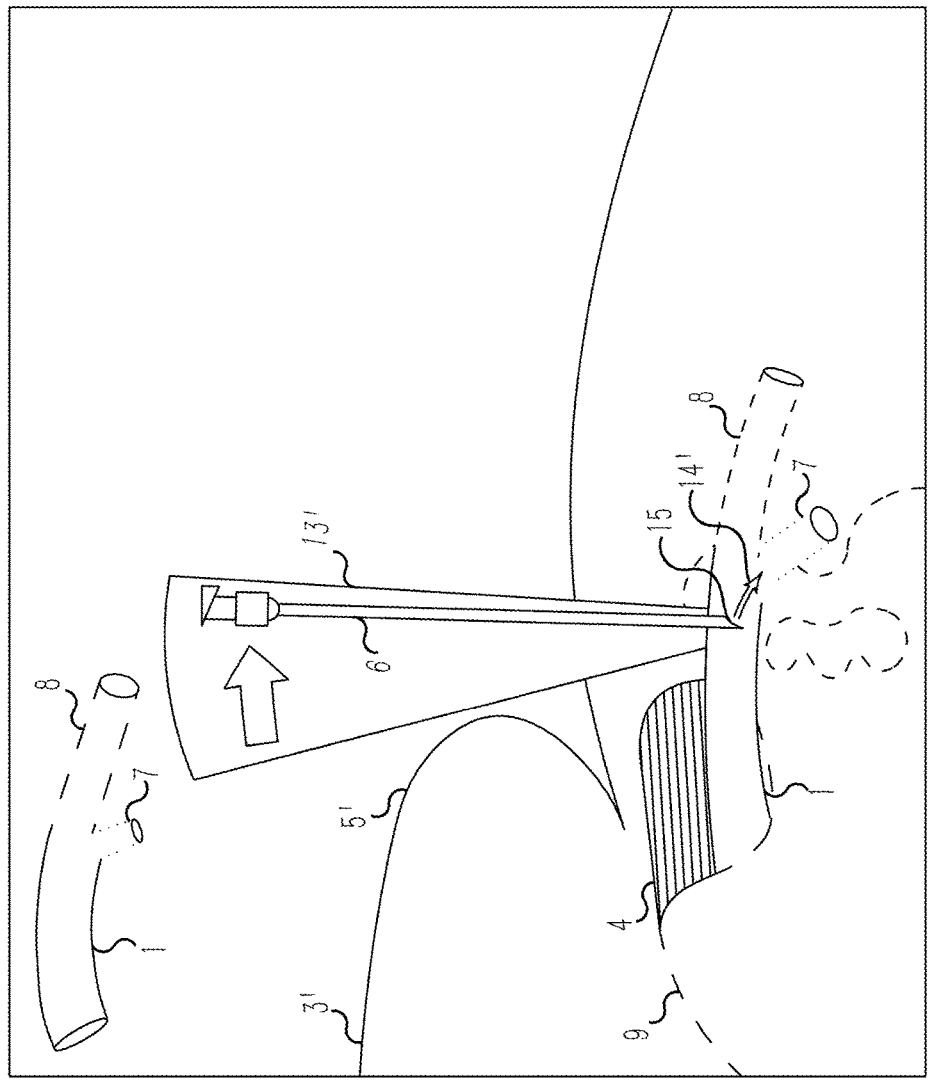
FIG. 4C shows the wire extrusion vector in the antegrade-stick approach.
Figure 5A:
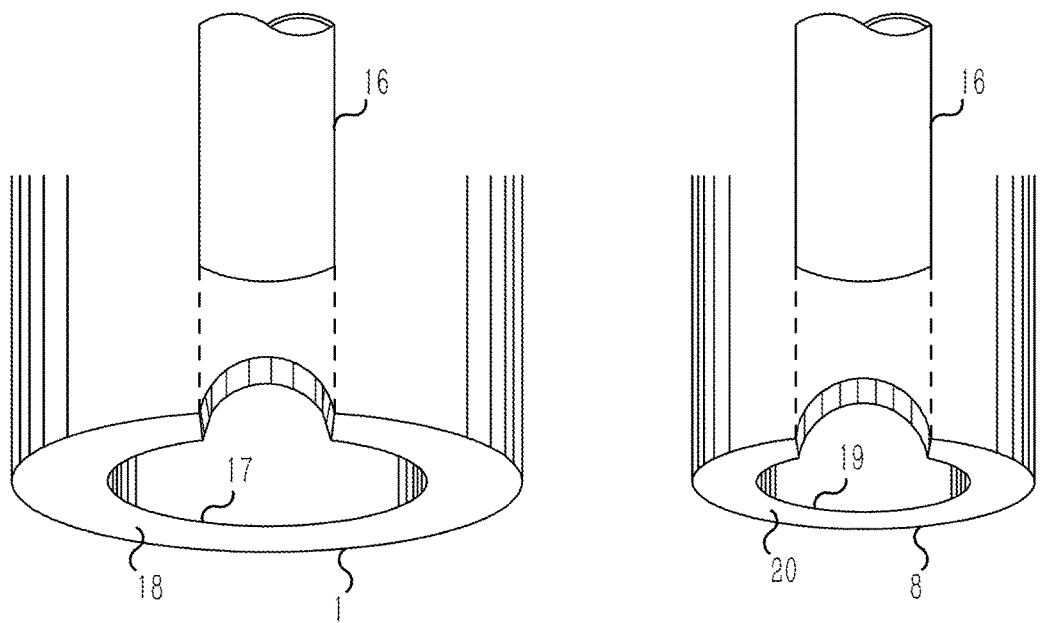
FIG. 5A shows a perspective view of arteriotomy comparisons between the CFA and the SFA.
Figure 5B:
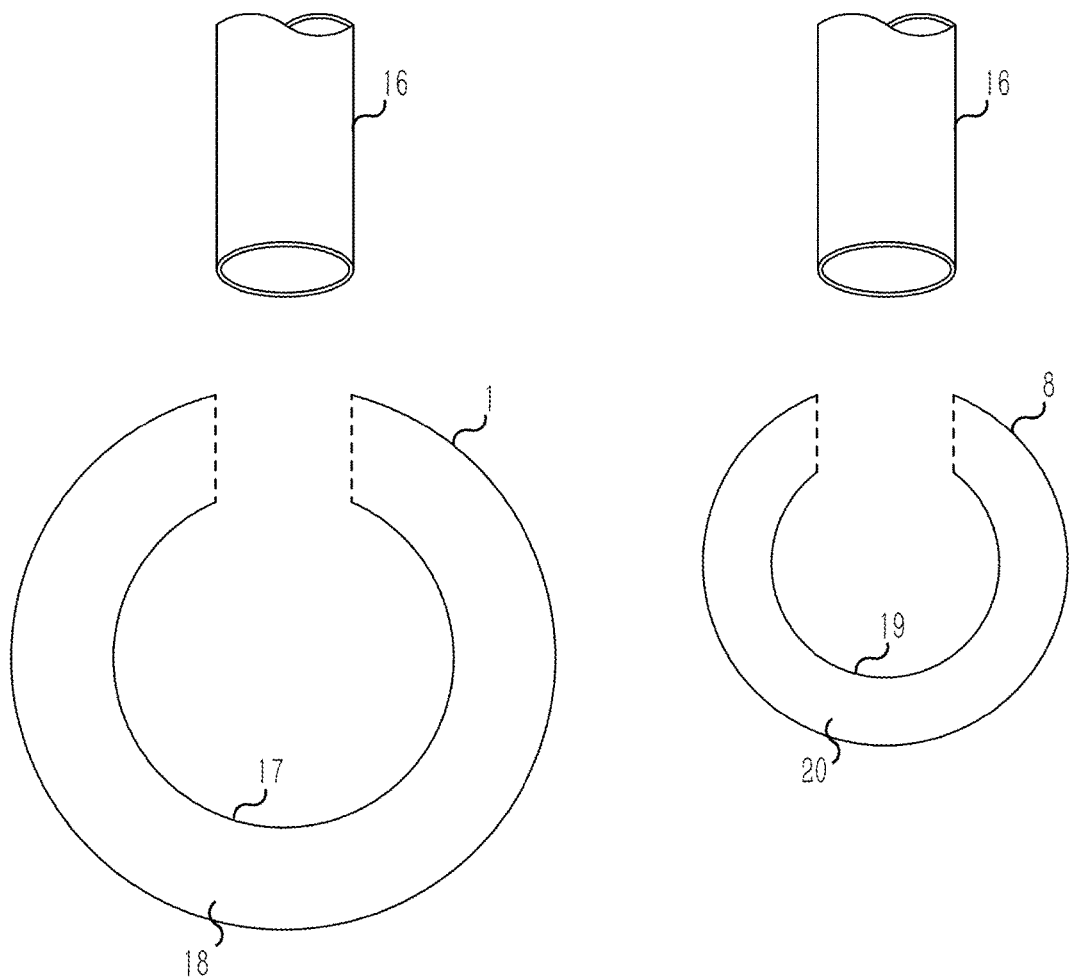
FIG. 5B shows an elevation view of arteriotomy comparisons between the CFA and the SFA.
Figure 6:
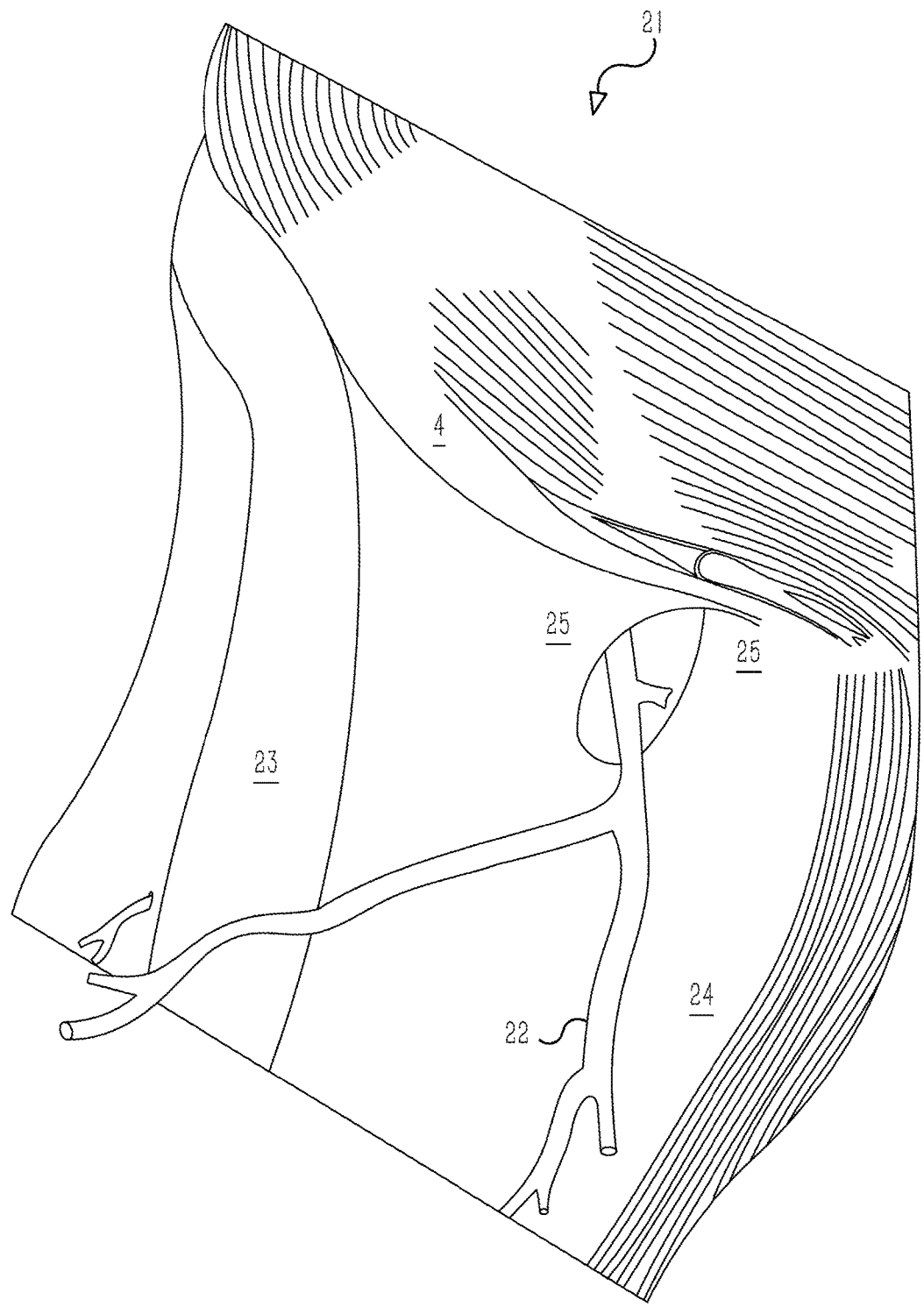
FIG. 6 shows the femoral triangle.
Figure 7:
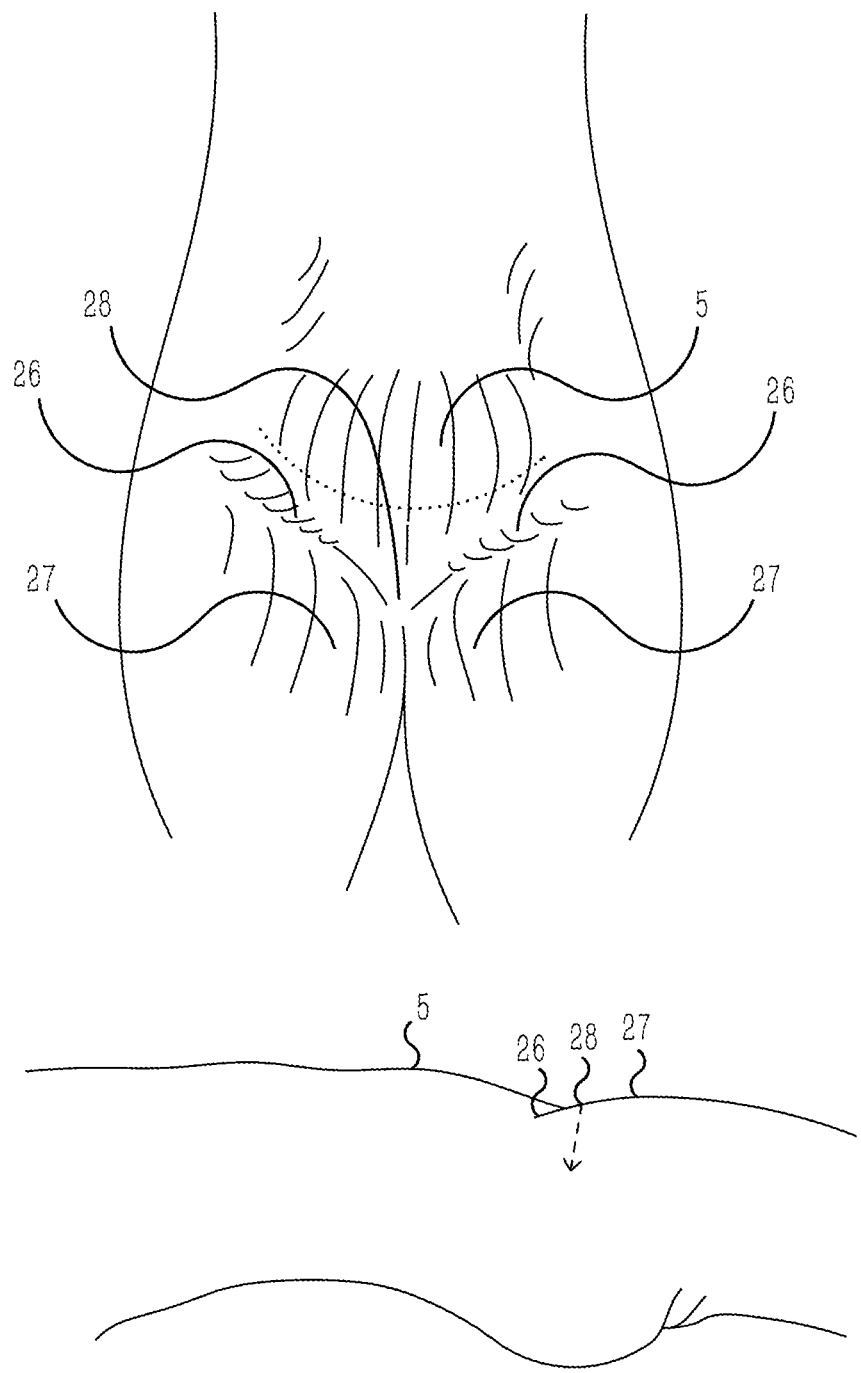
FIG. 7 shows body surface planes and curvatures.

To assist in the understanding of the present disclosure the following list of components and associated numbering found in the drawings is provided herein:

Table of Components

| Component | # |
|---|---|
| Common Femoral Artery (CFA) | 1 |
| Target Segment | 2 |
| Target Segment | 2' |
| Body | 3 |
| Body | 3' |
| Inguinal Ligament | 4 |
| Abdominal Protuberance | 5 |
| Needle | 6 |
| Profunda Femoris Artery (PFA) | 7 |
| Superficial Femoral Artery (SFA) | 8 |
| Anterior Superior Iliac Spine (ASIS) | 9 |
| Right Femur | 10 |
| Femoral Head | 11 |
| Coccyx | 12 |
| Swath | 13 |
| Swath | 13' |
| Wire-Extrusion Vector | 14 |
| Wire-Extrusion Vector | 14' |
| Needle Bore | 15 |
| 8 French Sheath | 16 |
| Lumen | 17 |
| Wall Thickness | 18 |
| Lumen | 19 |
| Wall Thickness | 20 |
| Femoral Triangle | 21 |
| Femoral Vein | 22 |
| Sartorius Muscle | 23 |
| Adductor Longus Muscle | 24 |
| Fascia Lata | 25 |
| Transverse Groove | 26 |
| Muscular Curvature | 27 |
| Sub-Pubic Pit | 28 |
| Operator | 29 |
| Patient | 30 |
| C-Arm X-Ray Machine | 31 |
| Monitors | 32 |
| Ultrasound Transducer | 33 |
| Gel | 34 |
| Skin | 35 |
| Blood | 36 |
| First Wire | 37 |
| External Iliac Artery (EIA) | 38 |
| Arrow | 39 |
| Micro-Puncture Dilator | 40 |
| Sheath | 41 |
| Arrow | 42 |
| Arrows | 43 |
| Arrow | 44 |
| Second Wire | 45 |
| Arrows | 46 |
| Curved Needle | 47 |
| Arrow | 48 |
| Arrow | 49 |
| Arrows | 50 |
| "A" Wire | 51 |
| Arrow | 52 |
| Arrow | 53 |

-continued

Table of Components

| Component | # |
|---|---|
| Arrow | 54 |
| Arrows | 55 |
| Dual-Lumen Access Director (DAD) | 56 |
| Arrows | 57 |
| "A" Wire Lumen | 58 |
| "D" Wire Lumen | 59 |
| Oval Orifice | 60 |
| Female Luer Head | 61 |
| Arrow | 62 |
| Arrow | 63 |
| "D" Wire | 64 |
| Arrow | 65 |
| Injection Seal And Side-Port | 66 |
| J-Tip | 67 |
| Arrows | 68 |
| Fingers | 69 |
| Arrow | 70 |
| Angiographic Sheath | 71 |
| Needle Control Hub | 72 |
| Wire Entry Orifice | 73 |
| Radius | 74 |
| Lumen | 75 |
| Dilator | 76 |
| Dilator Hub | 77 |
| Tip Segment | 78 |
| Larger Diameter Segment | 79 |
| Taper Segment | 80 |
| Bump | 81 |
| Dip | 82 |

DETAILED DESCRIPTION

Retrograde Entry Antegrade Placement (REAP™) for SFA Access

The following will describe various apparatus and various method steps utilized in retrograde entry for antegrade placement of endovascular devices via SFA access.

Figure 8:
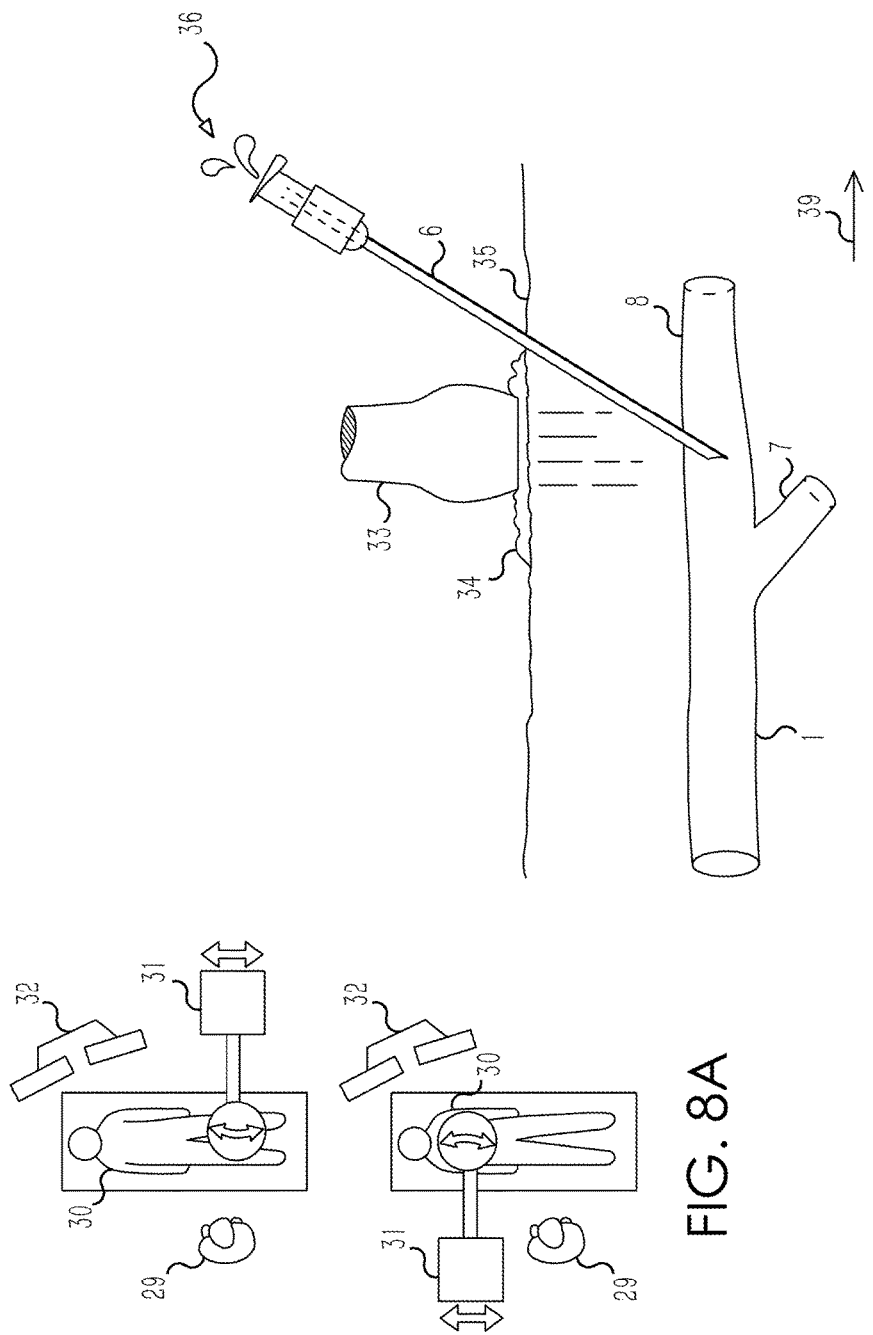
FIG. 8A shows the operator, patient, and equipment in alternate positions.
FIG. 8B shows an ultrasound-guided micro-puncture entry into the SFA.

Step 1. FIG. 8A shows the operator, patient, and equipment in alternate positions. Referring now to FIG. 8A, Operator 29 is positioned on Patient 30's right side, as for any traditional femoral artery entry angiographic procedure. The C-Arm X-Ray Machine 31 may be positioned opposite or adjacent to Operator 29 and is movable in the directions indicated by the arrows. C-Arm X-Ray Machine 31 is used to perform fluoroscopic and angiographic imaging. Monitors 32 are positioned at the patient's left, at torso level. Referring now to FIG. 8B, ultrasound is used to acquire data including the distance from Skin 35 to CFA 1, the lumen diameter of CFA 1, and location of the orifice of the take-off of PFA 7 and the location of the origin of CFA 1. Operator 29 utilizing palpation and Ultrasound Transducer 33 with ultrasound transmission Gel 34 sticks Needle 6 through the Skin 35 at an entry point and makes an ultrasound-guided micro-puncture entry into SFA 8 at a point 1-2 cm distal from the origin of SFA 8, with Needle 6 directed in the traditional retrograde position (see FIG. 1B). Blood 36 bleeds back from Needle 6 indicating to Operator 29 that the tip of Needle 6 has punctured SFA 8. Arrow 39 indicates the direction of blood flow antegrade. In one embodiment, Needle 6 is 18-gauge, but other gauge needles may also be used.

Figure 9:
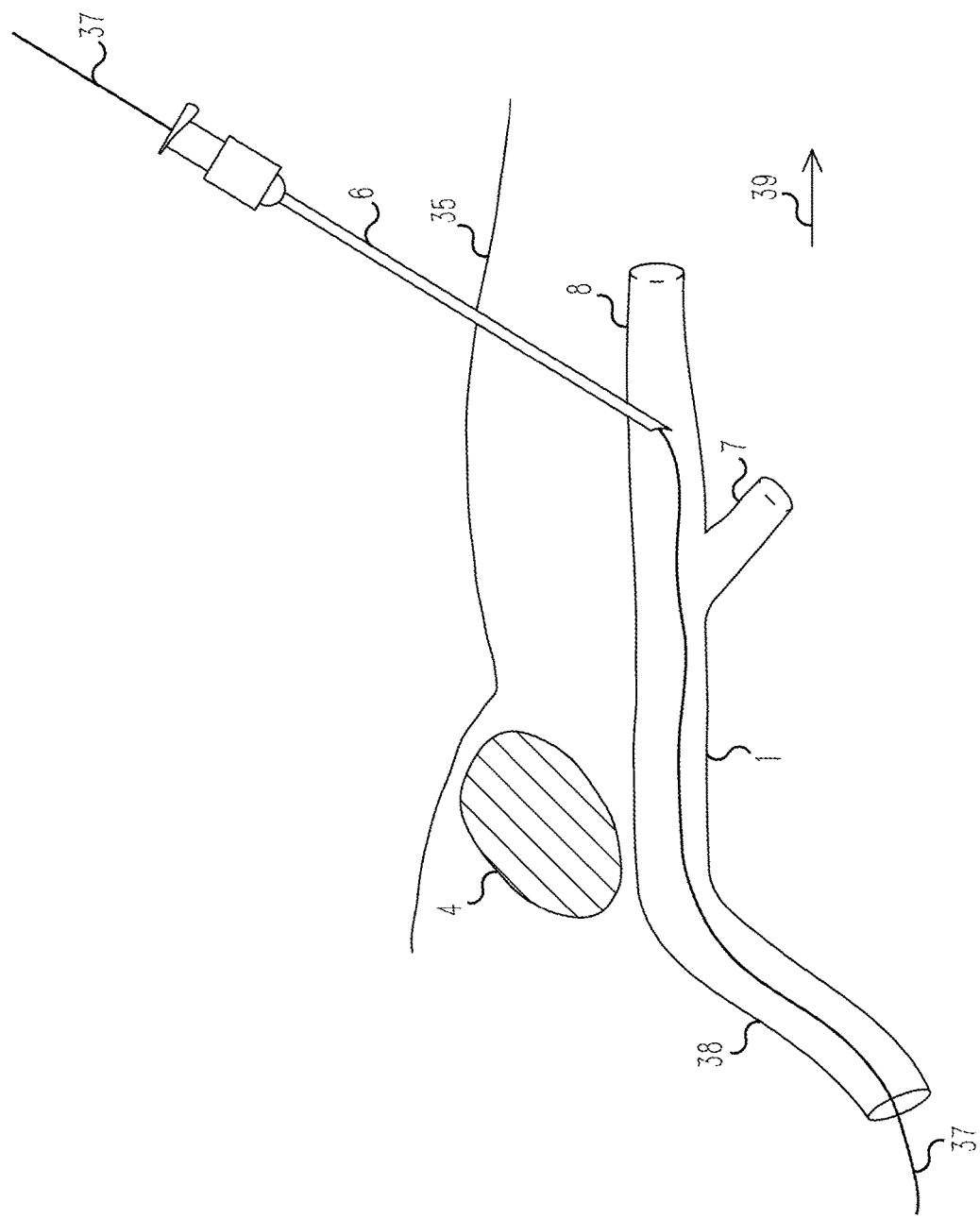
FIG. 9 shows advancing a wire into the iliac system.

Step 2. FIG. 9 shows advancing a first wire into the iliac system. Referring now to FIG. 9, First Wire 37 (in one embodiment, about 0.014-inch in diameter) is advanced through Needle 6 into EIA 38 of the iliac system and confirmed by fluoroscopy with C-Arm X-Ray Machine 31. Needle 6 is then removed.

Figure 10:
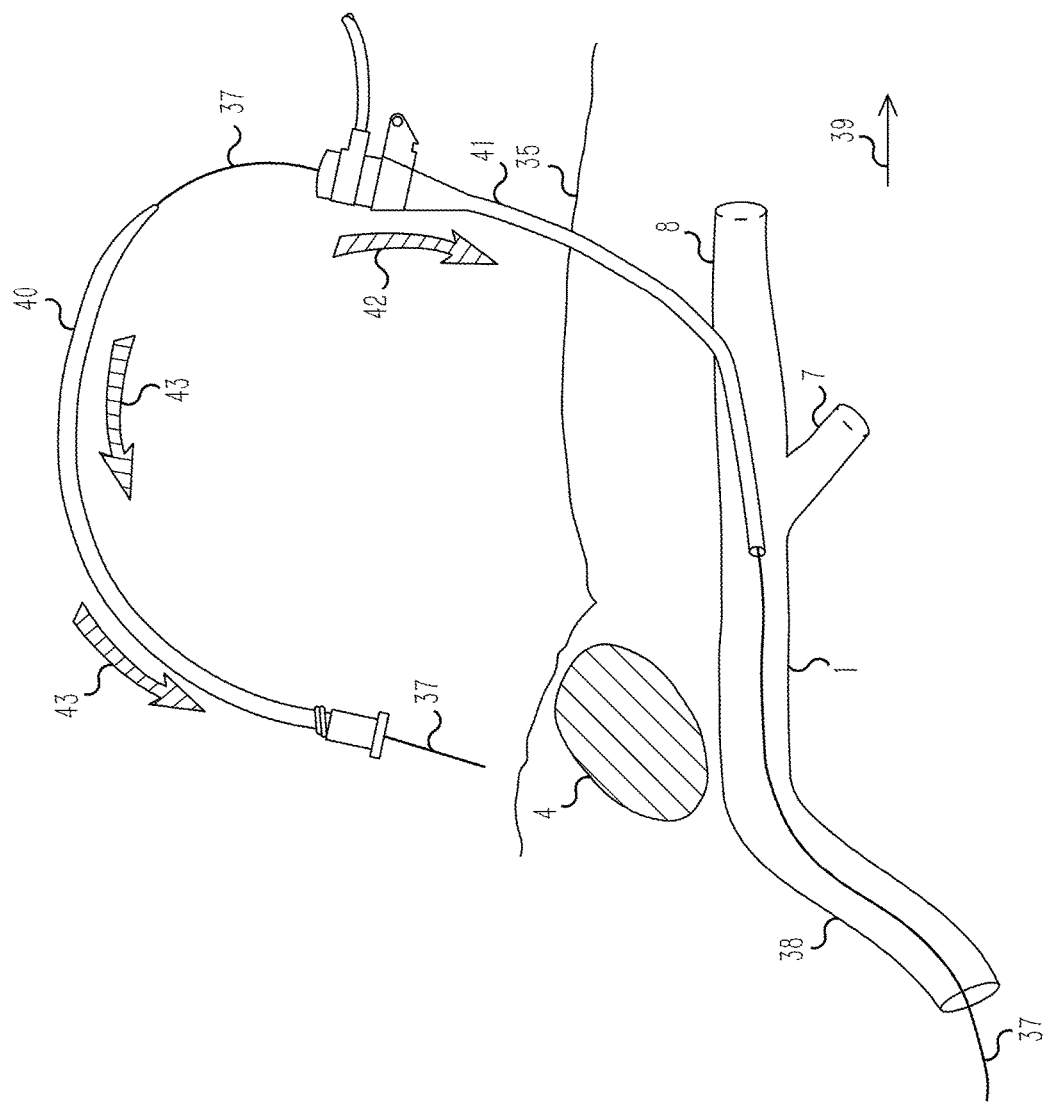
FIG. 10 shows advancing the dilator and sheath, and then removing the dilator.

Step 3. [Optional] FIG. 10 shows advancing the dilator and sheath and then removing the dilator. Referring now to FIG. 10, Micro-Puncture Dilator 40 (typically 3 French, but other sizes may be used) inside Sheath 41 is passed over First Wire 37 and into SFA 8 in the direction indicated by Arrow 42. The Micro-Puncture Dilator 40 is then removed in the direction indicated by Arrows 43 leaving Sheath 41 in place.

Figure 11:
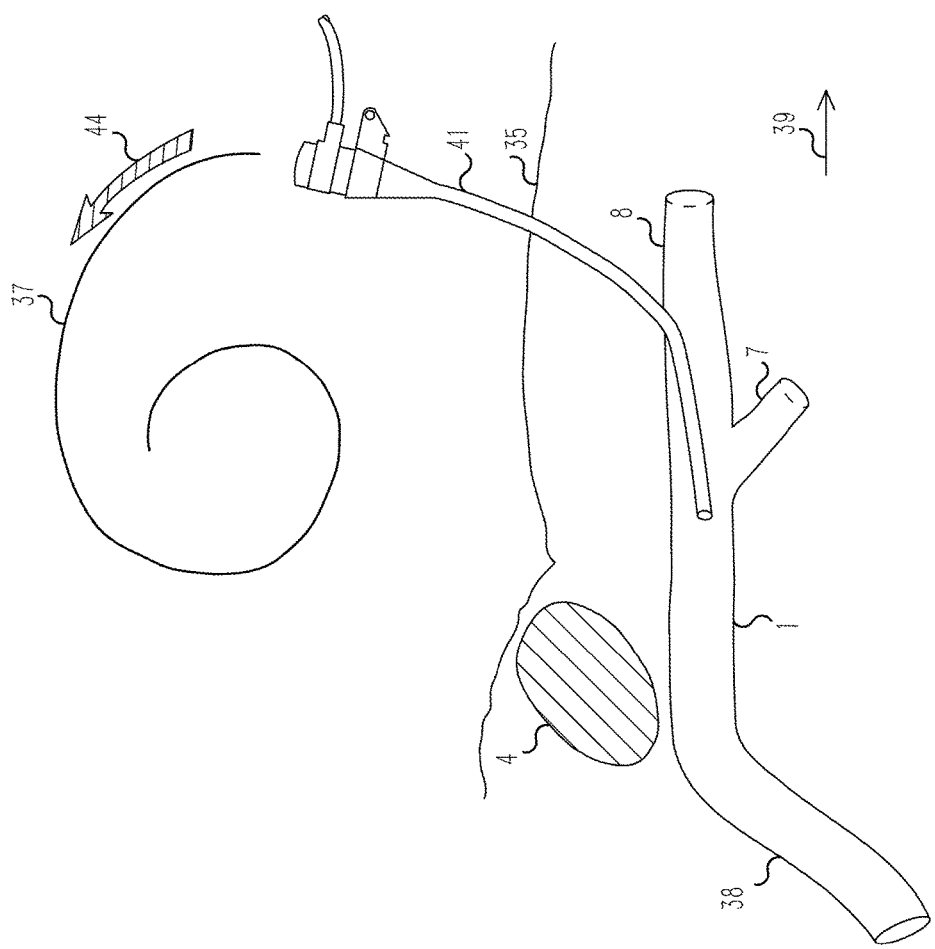
FIG. 11 shows the first wire being removed.
Figure 12:
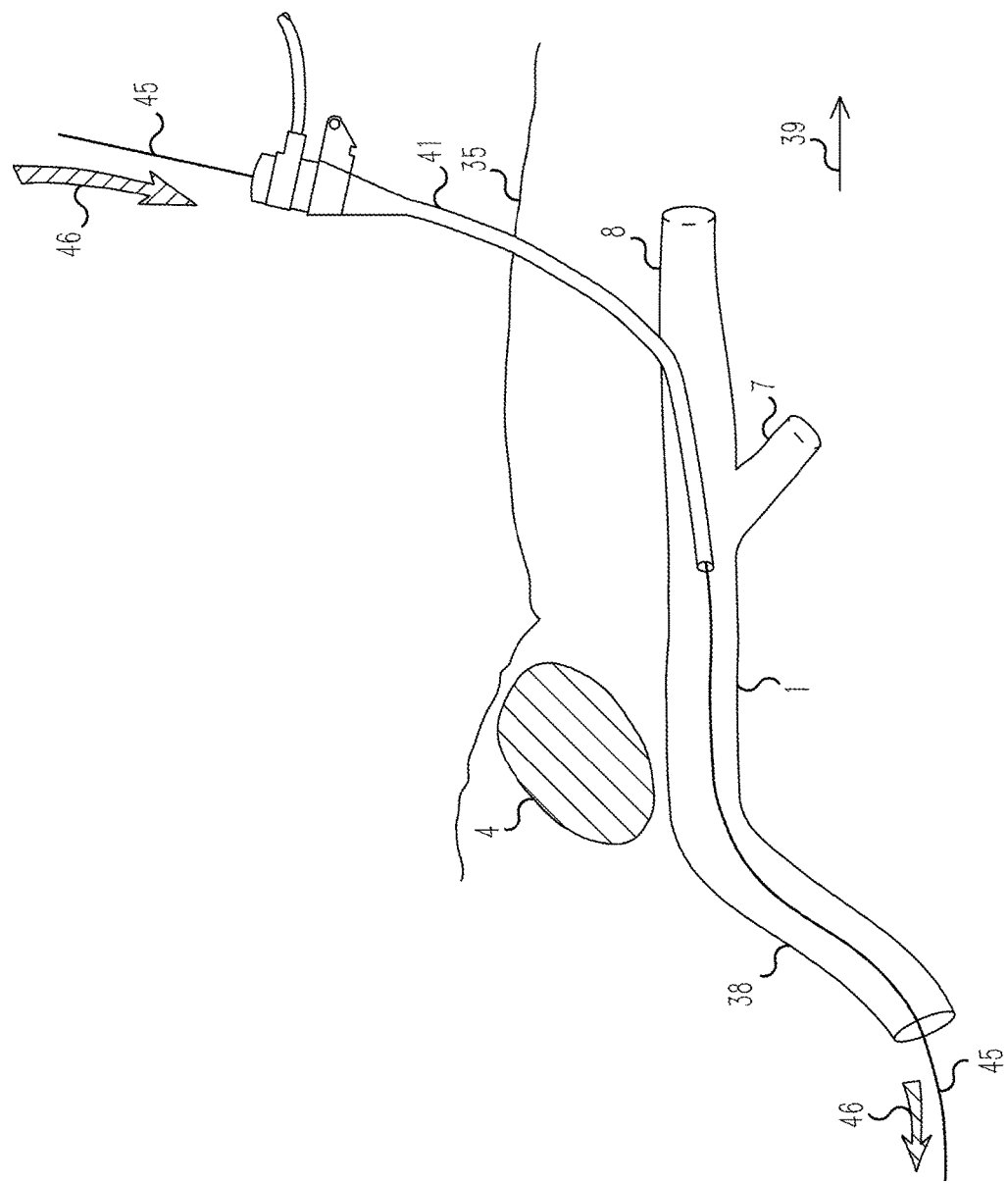
FIG. 12 shows a second wire being inserted.

Step 4. [Optional] Referring now to FIG. 11, First Wire 37 is removed in the direction indicated by Arrow 44. Referring now to FIG. 12, Second Wire 45 (in one embodiment, Second Wire 45 is about 0.035-inch in diameter) is inserted into Sheath 41 in the direction indicated by Arrows 46 and into EIA 38 and confirmed by fluoroscopy with C-Arm X-Ray Machine 31. Sheath 41 is then removed from SFA 8 over Second Wire 45 in a direction opposite to Arrows 46. In another embodiment, Second Wire 45 is used at the outset instead of First Wire 37 in Step 2 above.

In an alternative embodiment, the micro-puncture kit described above is not used. Instead, a larger needle, such as an 18-gauge needle, is used to puncture the skin and enter SFA 8 and then Second Wire 45 is inserted through the lumen of the larger needle and into SFA 8. Steps 1-4 can be replaced with the following optional Steps 1' and 2'.

Step 1'. [Optional] Referring now to FIG. 8B, ultrasound is used to acquire data including the distance from Skin 35 to CFA 1, the lumen diameter of CFA 1, and identification of the orifice of the take-off of PFA 7 and of the origin of CFA 1. Operator 29 utilizing palpation and Ultrasound Transducer 33 with ultrasound transmission Gel 34 sticks Needle 6 through the Skin 35 at an entry point and makes an ultrasound-guided entry into SFA 8 at a point 1-2 cm distal from the origin of SFA 8, with Needle 6 directed in the traditional retrograde position. Blood 36 bleeds back from Needle 6 indicating to Operator 29 that the tip of Needle 6 has punctured SFA 8. Arrow 39 indicates the direction of blood flow antegrade.

Step 2'. [Optional] FIG. 9 shows advancing a wire into the iliac system. Referring now to FIG. 9, Second Wire 45 is advanced through Needle 6 into EIA 38 of the iliac system and confirmed by fluoroscopy with C-Arm X-Ray Machine 31. Needle 6 is then removed.

Figure 13:
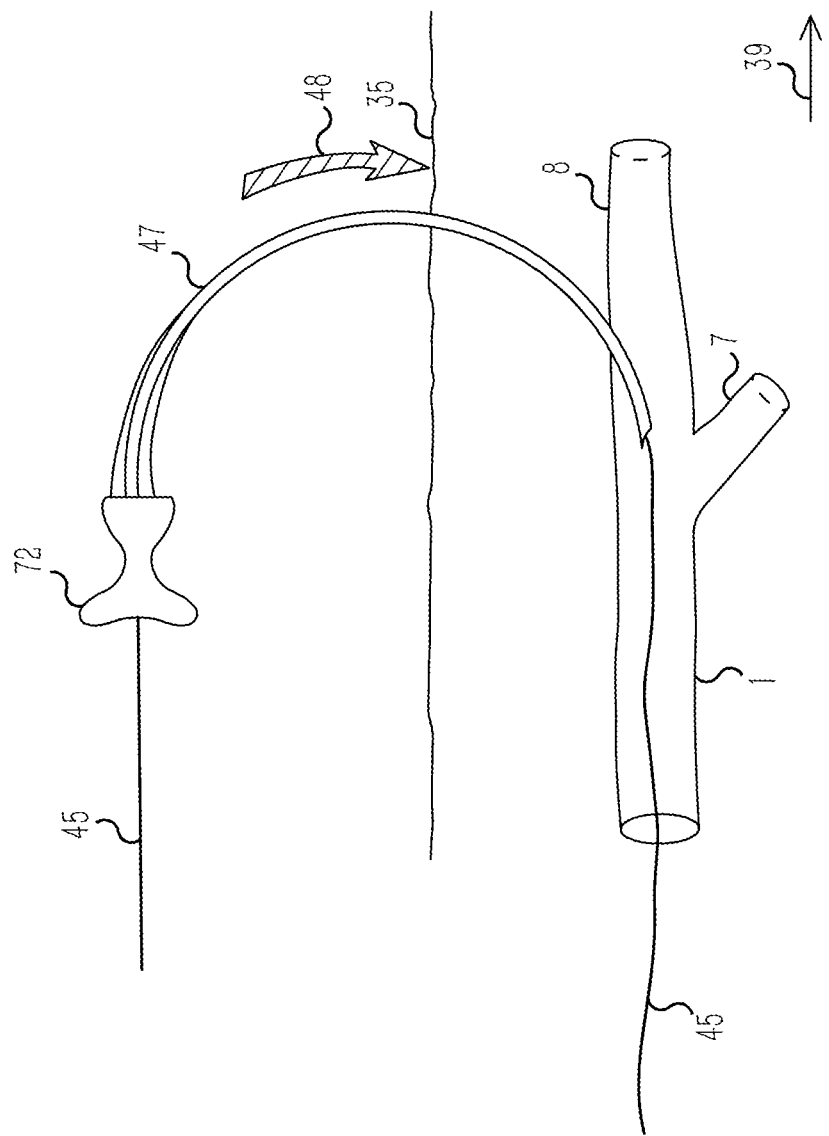
FIG. 13 shows a curved needle being advanced over the second wire.

Step 5. FIG. 13 shows a curved needle being advanced over the second wire. Referring now to FIG. 13, Curved Needle 47 is advanced in the direction indicated by Arrow 48 over Second Wire 45 to the point where the aim of the tip is substantially horizontal or parallel to SFA 8 and CFA 1. Curved Needle 47 may be of various lengths and with different radii in order to accommodate specific patient anatomy. Needle length and radii are determined from the ultrasound analysis done in step 1 (see FIG. 8B).

In another embodiment, Steps 1-4 and 5 and/or Steps 1', 2', and 5 can be replaced with the following step.

Figure 14:
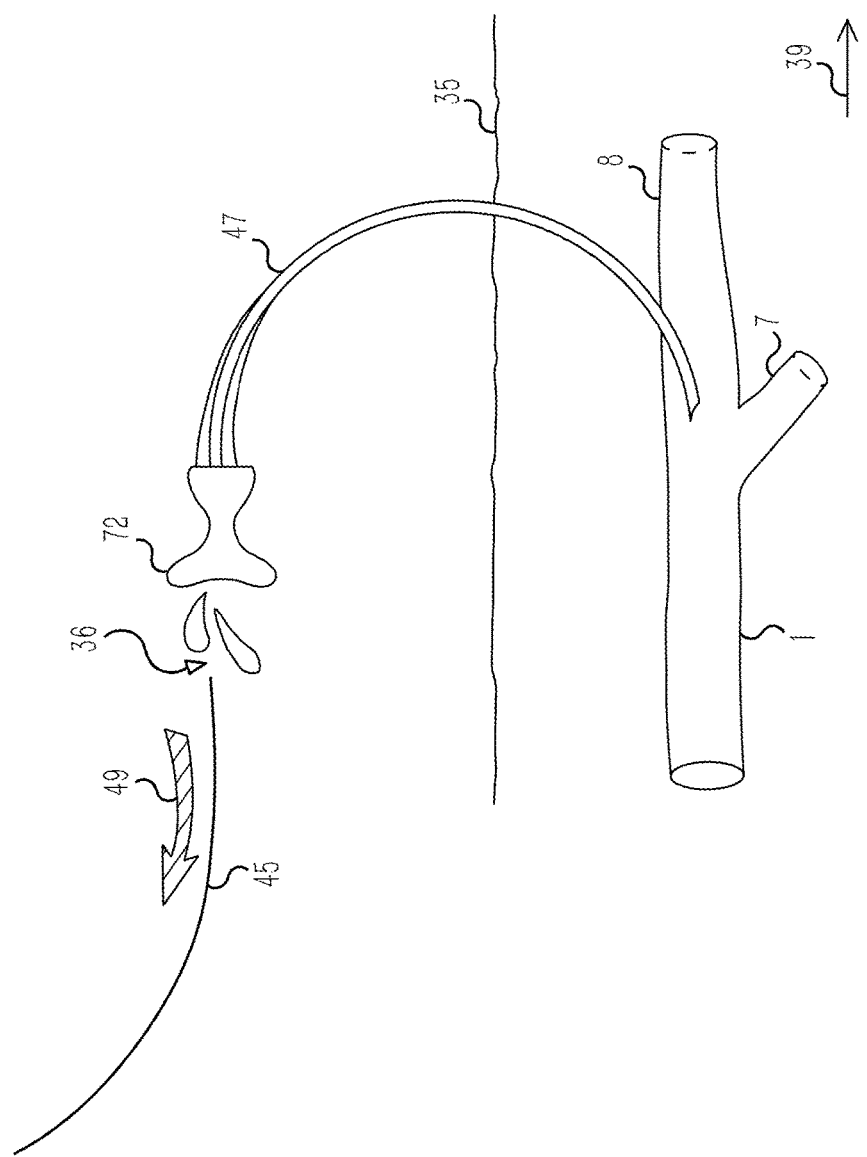
FIG. 14 shows the second wire being removed completely.

Step 1" Operator 29 utilizing palpation and Ultrasound Transducer 33 with ultrasound transmission Gel 34 (as shown in FIG. 8B) sticks Curved Needle 47 through the Skin 35 at an entry point and makes an ultrasound-guided entry into SFA 8 at a point 1-2 cm distal from the origin of SFA 8, with Curved Needle 47 directed in the traditional retrograde position (see FIG. 14). Blood 36 bleeds back from Curved Needle 47 indicating to Operator 29 that the tip of Curved Needle 47 has punctured SFA 8. Arrow 39 indicates the direction of blood flow antegrade. The method continues with Step 6 below.

Figure 30:
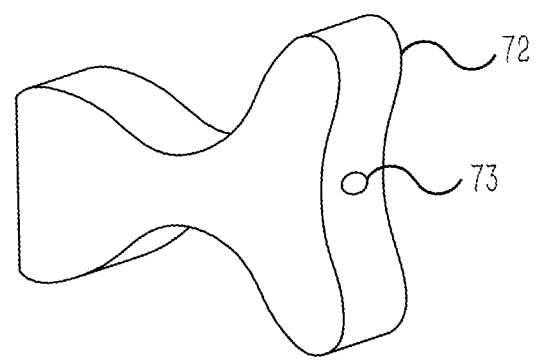
FIG. 30 shows the needle control hub.

FIG. 30 shows the needle control hub. Referring now to FIG. 30, Needle Control Hub 72 is designed to facilitate hand motions required for arterial exit and post exit maneuvers. In endovascular diagnostic and therapeutic work, the usual arterial access needle hub is designed for the purpose of pushing the straight needle in the straight direction towards an endpoint target which has depth, width and breadth, into which the needle tip must enter and then dwell momentarily while a wire is passed through the needle into the lumen of the artery. In the REAP™ method, Curved Needle 47 must track along the same course into the SFA 8 lumen already occupied by the previously placed Second Wire 45, and then must exit CFA 1 and track up a curvilinear pathway which has continually varying directionality and is aimed at a topographic landmark guided by Operator 29's palpation. For this reason, Needle Control Hub 72, i.e., the control point of the Operator 29's hand upon Curved Needle 47, must be somewhat bulkier and shaped to allow precise upward movement and side-to-side deflection of the needle tip. Wire Entry Orifice 73 aligns with the lumen of Curved Needle 47. Needle Control Hub 72 is linked to a stiffened and tapering segment of needle diameter.

Figure 31:
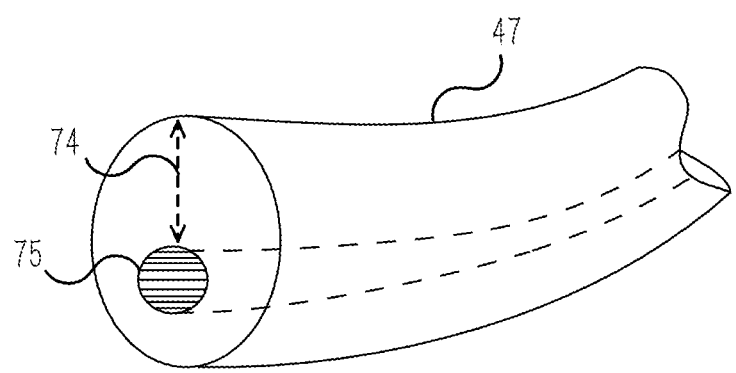
FIG. 31 shows a portion of the curved needle.

FIG. 31 shows a portion of the curved needle. Referring now to FIG. 31, certain metallurgical and strengthening and other modifications of Curved Needle 47 are shown. Because of the upward and curvilinear vectors of force applied to Curved Needle 47, it must be modified in its manufacture for the purpose of strengthening its resistance to deformity during upward tip deflecting maneuvers for arterial exit and subsequent tracking towards the skin surface. Thickening of an inner portion of the peri-lumenal Radius 74 of the needle in a tapered fashion beginning at the hub is one such method of strengthening, along with metallurgical compositional alterations to provide more anti-deformational strength along the long-axis of the curvature. The Lumen 75 is located in the outer portion of Curved Needle 47 for additional strength. The needle tip is also modified to alter its sharpening in order to focus sharpness at a position at the tip alone of its bevel, not circumferential around the bevel. This is designed to allow effective puncture of the arterial endothelial surface and arterial wall as well as tissue planes leading to and including the skin.

Step 6. FIG. 14 shows the second wire being completely removed. Referring now to FIG. 14, Second Wire 45 is withdrawn in the direction indicated by Arrow 49 completely out of Curved Needle 47, and Blood 36 bleeds back from the Lumen 75 of Needle Control Hub 72 of Curved Needle 47.

Figure 15:
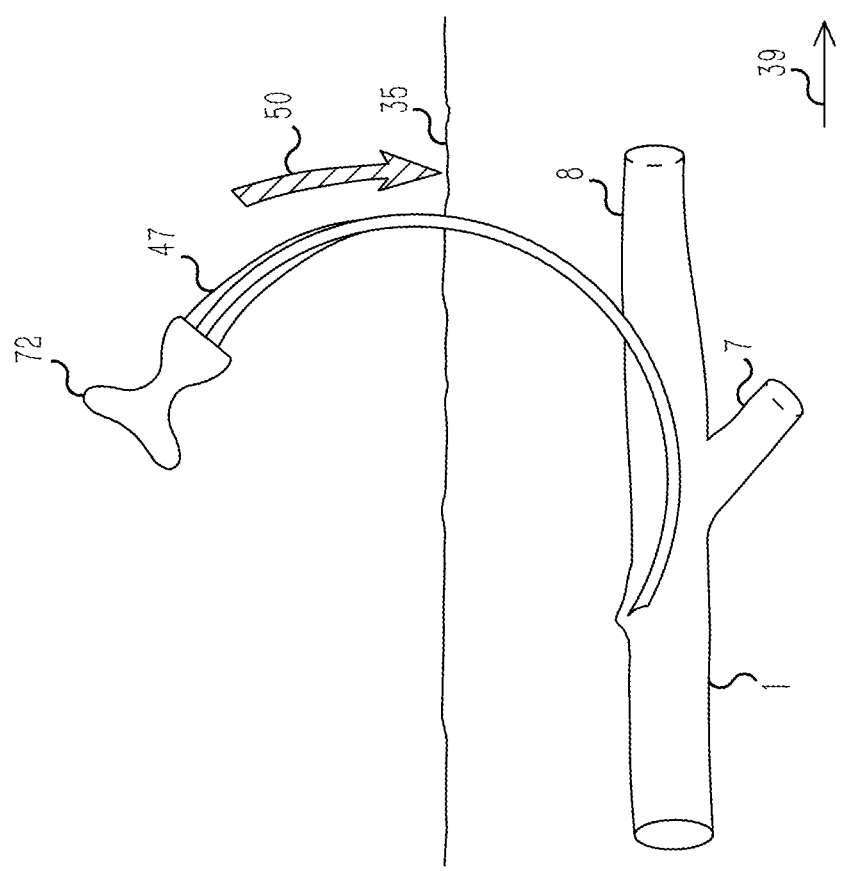
FIG. 15 shows the curved needle being advanced retrograde within the CFA.

Step 7. FIG. 15 shows the curved needle being advanced retrograde within the CFA. Referring now to FIG. 15, following its own curvature in a simple circular track in the direction indicated by Arrow 50, Curved Needle 47 is advanced retrograde within the lumen of CFA 1.

Step 8. Still referring to FIG. 15, advancement continues and bleed-back ceases when Operator 29 feels Curved Needle 47 traverse the arterial wall of CFA 1.

Figure 16:
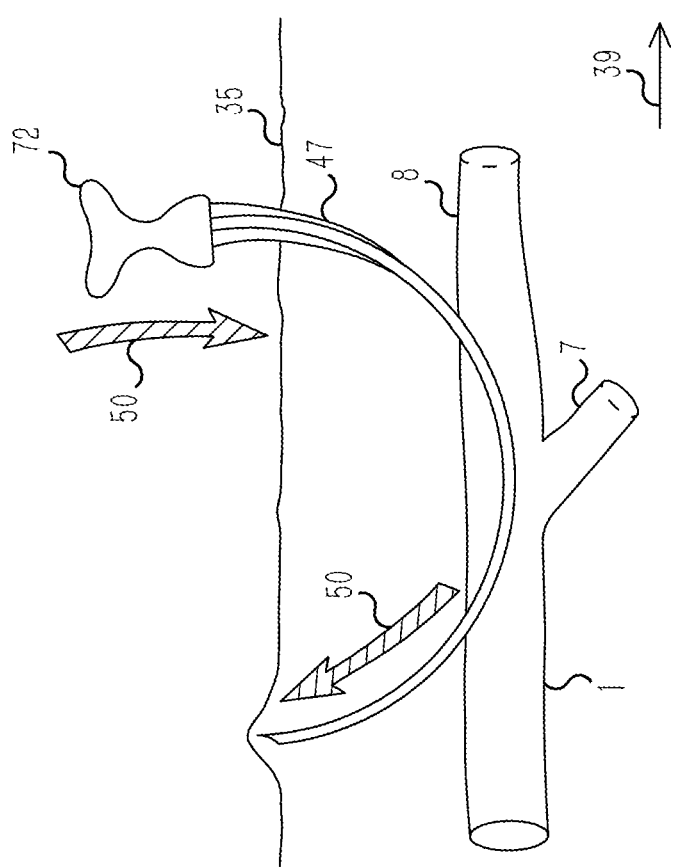
FIG. 16 shows the curved needle exiting the CFA and the skin.

Step 9. FIG. 16 shows the curved needle exiting the CFA and the skin. Referring now to FIG. 16, Curved Needle 47 continues to track along its semicircular pathway towards Skin 35 at a site targeted by Operator 29, tenting up the dermis, and the bevel of the tip of Curved Needle 47 is pushed through Skin 35 at an exit point. An armored transparent gel pad (not shown in FIG. 16) can be used to receive the bevel if tenting is not prominent, protecting Operator 29's fingers.

Figure 17:
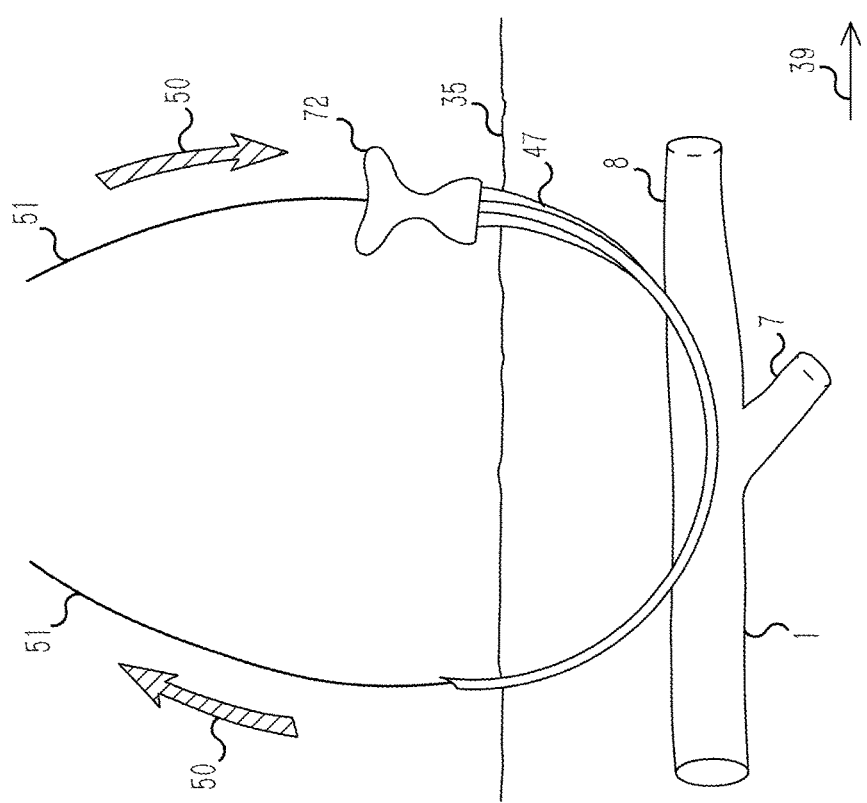
FIG. 17 shows a short A wire passed through the curved needle "air-to-air."

Step 10. FIG. 17 shows a short "A" wire passed through the curved needle "air-to-air." Referring now to FIG. 17, "A" Wire 51 (typically 0.014-inch in diameter) is passed through Curved Needle 47 in the direction indicated by Arrows 50. This is termed an "air-to-air" wire, in that both ends are non-lumenal, although the mid-portion of the wire traverses the CFA 1/SFA 8 lumenal region. The air-to-air wire is a position-holding device used for precise placement of the Dual-Lumen Access Director (DAD) 56 (see FIG. 20).

Figure 18A:
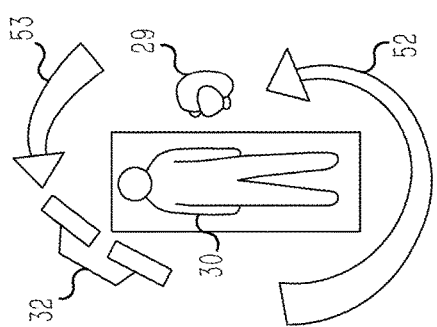
FIG. 18A shows the change in position of the operator and monitors.
Figure 18B:
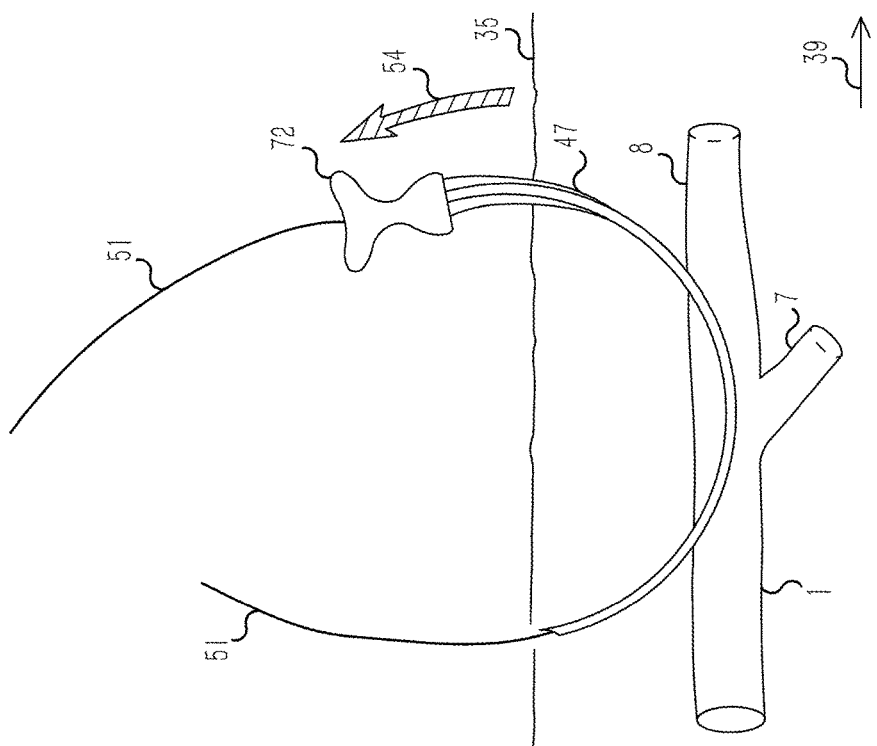
FIG. 18B shows the curved needle starting to be removed over the A wire.

Step 11. FIG. 18A shows the change in position of the operator and monitors. Referring now to FIG. 18A, Operator 29 moves in the direction indicated by Arrow 52 to the left side of Patient 30. Monitors 32 are swung in the direction indicated by Arrow 53 to the right of Patient 30 at waist level, opposite Operator 29. C-Arm X-Ray Machine 31 (not shown in FIG. 18A) continues to be based on the same side as it was at the beginning of the procedure, right or left (see FIG. 8A). Referring now to FIG. 18B, Curved Needle 47 starts to be removed over "A" Wire 51 in the direction indicated by Arrow 54.

Figure 19:
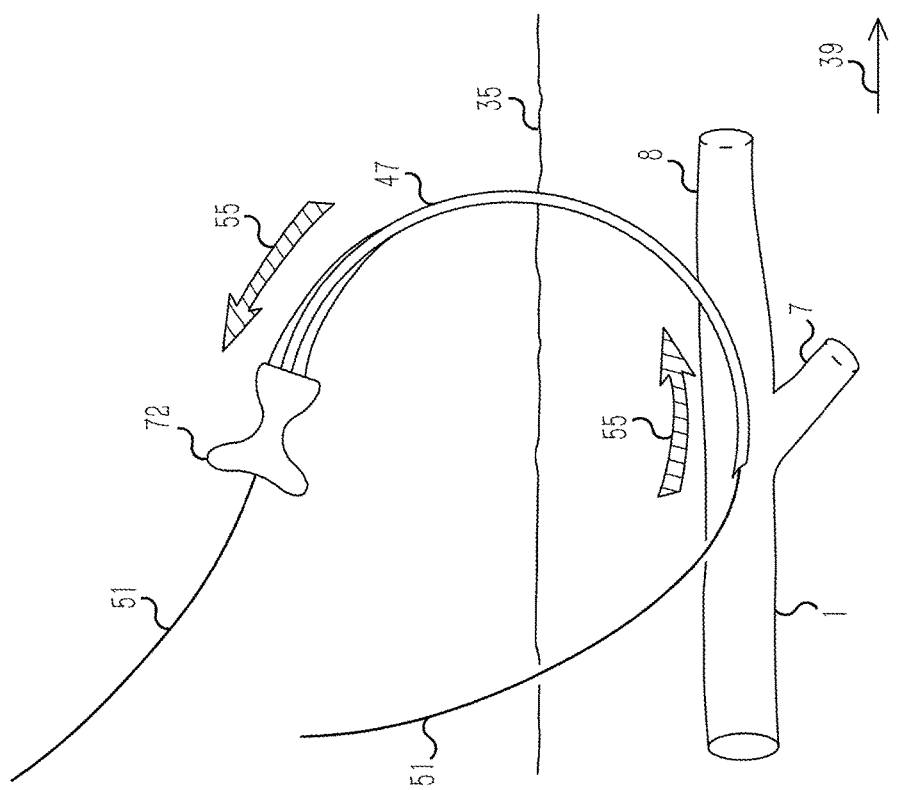
FIG. 19 shows the curved needle being removed over the A wire.

Step 12. FIG. 19 shows the curved needle being removed over the A wire. Referring now to FIG. 19, Curved Needle 47 is removed completely from CFA 1/SFA 8 lumenal region and Skin 35 over "A" Wire 51 in the direction indicated by Arrows 55.

Figure 20:
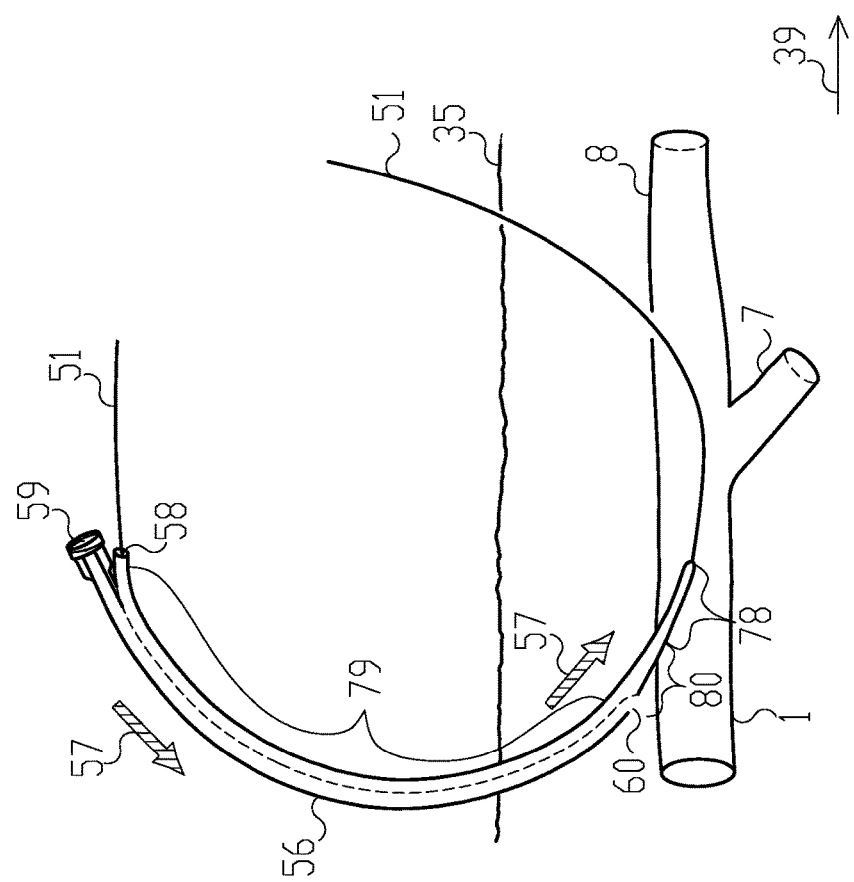
FIG. 20 shows the dual-lumen access director (DAD) advanced in the antegrade direction over the A wire and into the CFA lumen.

Step 13. FIG. 20 shows the Dual-Lumen Access Director (DAD) advanced in the antegrade direction over the A wire and into the CFA lumen. Referring now to FIG. 20, the Tip Segment 78 of DAD 56 is not so much "tapered" as it is a very slender cylinder whose "A" Wire Lumen 58 is sized to fit snugly over the "A" Wire 51. An advantage of this construction is that there is little to no bleed-back as the Tip Segment 78 follows over "A" Wire 51 into and out of the arterial wall of SFA 8. Tip Segment 78 must be pushed over "A" Wire 51 through the arterial wall twice—first as it enters the CFA 1 and then as it exits the SFA 8. For this reason, the leading 1-2 mm of Tip Segment 78 is progressively thinned to a leading cone shape comprising the exit for "A" Wire Lumen 58 to provide a smooth atraumatic profile of Taper Segment 80 and Tip Segment 78 as they pass through CFA 1, SFA 8, and into the tissue beyond SFA 8, minimizing the damage to CFA 1, SFA 8, and the tissue beyond SFA 8. In one embodiment, DAD 56 is made from a polymer.

As Tip Segment 78 exits the arterial wall of SFA 8 in preparation for passage of "D" Wire 64, protrusion of the narrow Tip Segment 78 through the arterial wall minimally enlarges that hole (which was originally created by previous passage of Curved Needle 47). "D" Wire 64 in one embodiment has hydrophilic properties.

Because the narrow cylindrical shape of Tip Segment 78 of DAD 56 must join with the Larger Diameter Segment 79 of DAD 56, there is in fact a Taper Segment 80 of DAD 56 between Tip Segment 78 and Larger Diameter Segment 79. Taper Segment 80 begins immediately distal to Oval Orifice 60. Taper Segment 80 is eccentric, so that the true centerlines of each of Tip Segment 78 and Larger Diameter Segment 79 it serves to join are not linear but are offset. Thus, there are two distinct diameters of DAD 56—a larger diameter of the longer Larger Diameter Segment 79 which ends in the eccentric Taper Segment 80, and onto a shorter smaller diameter Tip Segment 78. The Tip Segment 78 and Taper Segment 80 are intended to enter tissue after exiting the SFA 8, whereas the Larger Diameter Segment 79 is intended to remain intraluminal within SFA 8. DAD 56 thus has a smooth overall profile without excrescent orifice protrusions on any side. DAD 56 does not contain passage channels for treatment devices. DAD 56 contains two lumens, "A" Wire Lumen 58 and "D" Wire Lumen 59 that are sized only large enough to pass wires, and are not expandable lumens. "D" Wire Lumen 59 is designed to communicate with the vascular lumen/flow stream. "A" Wire Lumen 58 is designed to be an extravascular lumen that does not communicate with the vascular lumen/flow stream. Communicate as used above means activity or interaction that takes place within the vascular channel via a lumen of DAD 56. So, for "A" Wire Lumen 58, no wires are introduced into "A" Wire Lumen 58 that leave the lumen and pass into a vascular channel, such as CFA 1 or SFA 8 or PFA 7. For "D" Wire Lumen 59, wires are introduced into "D" Wire Lumen 59 that leave the lumen and do pass into a vascular channel, such as CFA 1 or SFA 8 or PFA 7. "A" Wire 51 and "A" Wire Lumen 58 provide a means of tethering DAD 56 in preparation for accurate vascular passage of "D" Wire 64 through "D" Wire Lumen 59. Thus, "A" Wire Lumen 58 does not communicate with the vascular lumen/flow stream, whereas "D" Wire Lumen 59 does. In this tethered position, DAD 56 will not twist or torque, assuring the correct alignment of the portions of DAD 56 within SFA 8.

Referring now again to FIG. 20, in the antegrade direction Operator 29 advances DAD 56 over "A" Wire 51 in the direction indicated by Arrows 57. DAD 56 has "A" Wire Lumen 58 that travels from an opening near Female Luer Head 61 to an opening in Tip Segment 78. DAD 56 is advanced over "A" Wire 51 through "A" Wire Lumen 58. The "A" Wire Lumen 58 does not have a fitting at the proximal end of DAD 56 which is at the opposite end from Tip Segment 78, as only the "A" Wire 51 passes through "A" Wire Lumen 58. "D" Wire Lumen 59 travels from Female Luer Head 61 to a point proximal to Taper Segment 80 that ends in Oval Orifice 60. DAD 56 has no natural curvature of its own but is flexible and will conform to the curvature of the "A" Wire 51 over which it is placed.

In one embodiment, DAD 56 has the following dimensions. DAD 56 has an overall length of about 160 mm. Larger Diameter Segment 79 has a length of about 140 mm, Taper Segment 80 has a length of about 12 mm, and Tip Segment 78 has a length of about 8 mm. The outside diameter of Larger Diameter Segment 79 is about 2.5 mm throughout its length and encompasses the "A" Wire Lumen 58 and "D" Wire Lumen 59. The outside diameter of the junction between Taper Segment 80 and Tip Segment 78 is about 0.9 mm. The 0.9 mm diameter of Tip Segment 78 is maintained throughout its length except for the cone shape at the tip of the Tip Segment 78 which is about 0.5 mm. The transition from the 2.5 mm diameter at the junction of the Larger Diameter Segment 79 and the Taper Segment 80 to the 0.9 mm diameter at the junction of the Taper Segment 80 and the Tip Segment 78 uniformly reduces the diameter of Taper Segment 80 along its length. This provides a smooth atraumatic profile of Tip Segment 78 and Taper Segment 80 as they pass through CFA 1, SFA 8, and into the tissue beyond SFA 8, minimizing the damage to CFA 1, SFA 8, and the tissue beyond SFA 8. Thus, two predominantly uniform in diameter cylinder portions (Larger Diameter Segment 79 and Tip Segment 78) are joined to each other by Taper Segment 80 that decreases in diameter along its length.

Taper Segment 80 and Tip Segment 78 encompass the "D" Wire Lumen 59 only. "A" Wire 51 has a diameter of about 0.36 mm and "A" Wire Lumen 58 is sized slightly larger, about 0.6 mm, to allow ease of movement of "A" Wire 51 within "A" Wire Lumen 58 but sized to also diminish bleed-back. "D" Wire 64 has a diameter of about 0.9 mm and "D" Wire Lumen 59 is sized slightly larger, about 1.2 mm, to allow ease of movement of "D" Wire 64 within "D" Wire Lumen 59 but sized to also diminish bleed-back. In viewing a cross-section of Larger Diameter Segment 79, the distance between the outer surface of the Larger Diameter Segment 79 to the outer circumference of the "A" Wire Lumen 58 is about 0.2 mm. The distance between the outer circumference of the "A" Wire Lumen 58 to the outer circumference of the "D" Wire Lumen 59 is about 0.2 mm. The distance between the outer circumference of the D" Wire Lumen 59 and the outer surface of the Larger Diameter Segment 79 is about 0.2 mm. One skilled in the art will recognize that other dimensions for DAD 56 are possible. In another embodiment, the diameter of the "A" Wire 51 and the "D" Wire 64 may be the same, and the diameter of the "A" Wire Lumen 58 and the "D" Wire Lumen 59 may be the same. One skilled in the art will recognize that other dimensions than those described above may be used according to specific needs and varying applications.

Figure 21:
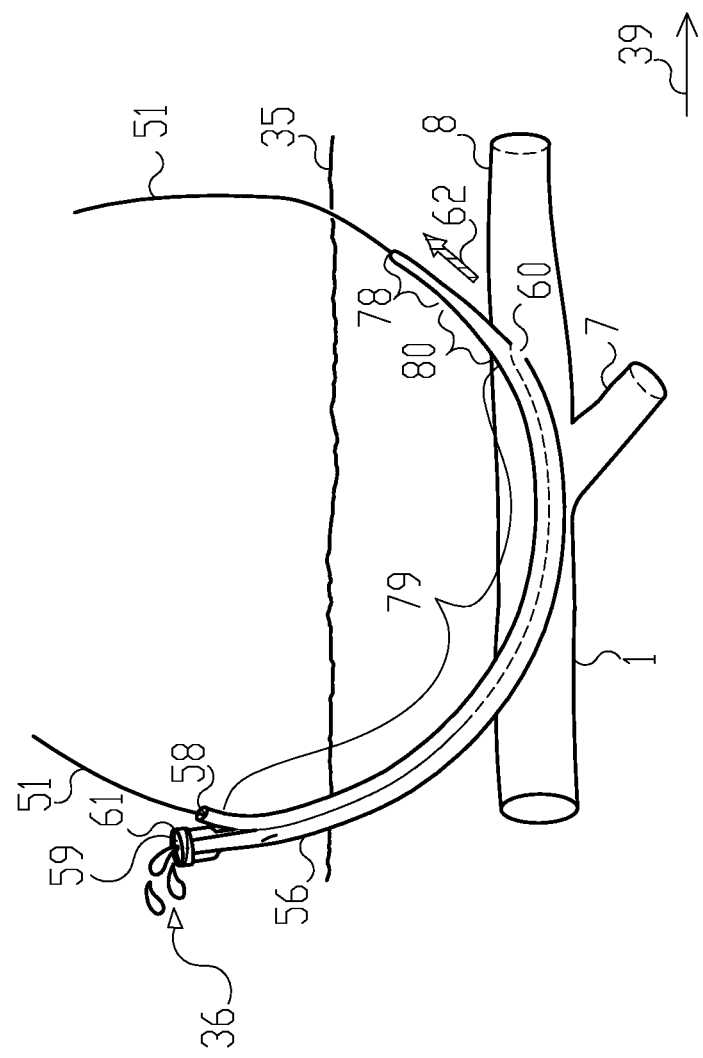
FIG. 21 shows bleed-back through the "D" wire lumen as the oval orifice of the DAD enters the CFA lumen.

Step 14. FIG. 21 shows bleed-back through the D wire lumen as the oval orifice of the DAD enters the CFA lumen. Referring now to FIG. 21, bleed-back of Blood 36 through "D" Wire Lumen 59 and exiting from Female Luer Head 61 of DAD 56 is observed by Operator 29 when Oval Orifice 60 of DAD 56 enters the lumen of CFA 1 in the direction indicated by Arrow 62. It is preferred that Tip Segment 78 not protrude out of Skin 35 in Steps 13-18, as this may unnecessarily enlarge the hole through the SFA 8 by Larger Diameter Segment 79.

Figure 22:
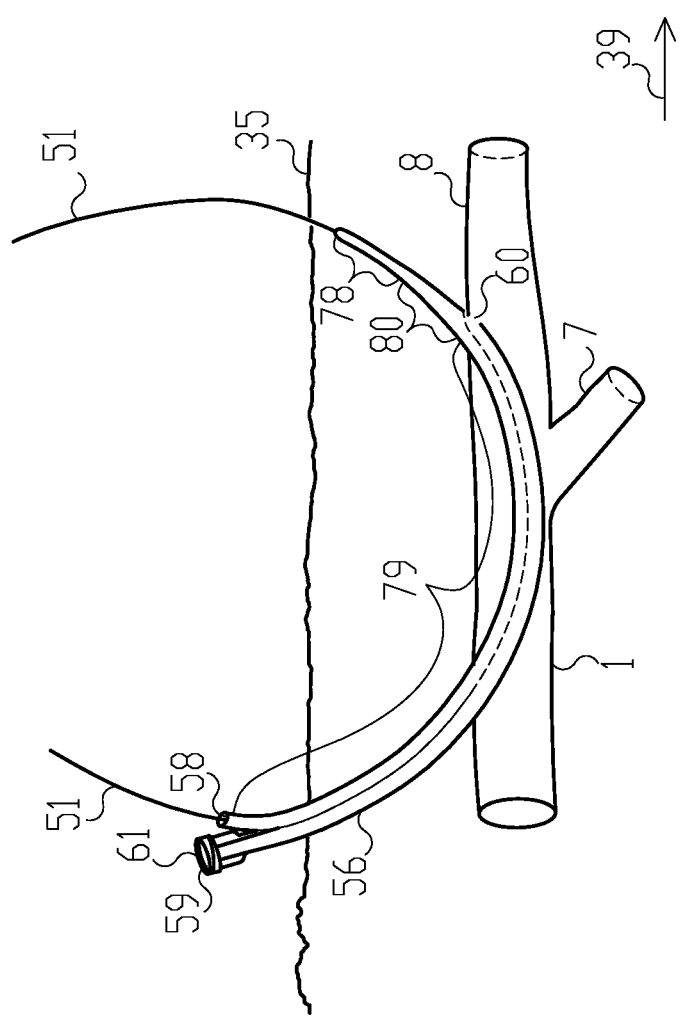
FIG. 22 shows the DAD further advanced, with bleed-back ceasing as the oval orifice is blocked.

Step 15. FIG. 22 shows the DAD further advanced, with bleed-back ceasing as the oval orifice is blocked. Referring now to FIG. 22, as DAD 56 is further advanced antegrade over "A" Wire 51 bleed-back ceases as Oval Orifice 60 is blocked by the wall of SFA 8 or by passing slightly beyond the wall of SFA 8 at the site of SFA 8 entry-arteriotomy.

Figure 23:
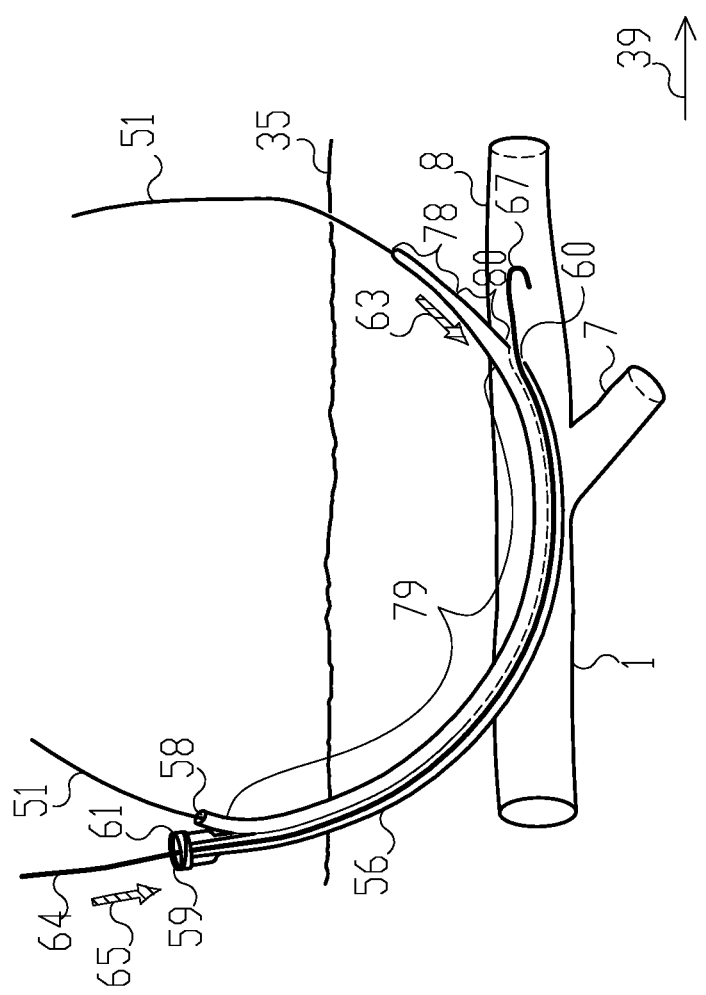
FIG. 23 shows the DAD being withdrawn a short distance in the retrograde direction, and the D wire inserted in the Luer head.

Step 16. FIG. 23 shows the DAD being withdrawn a short distance in the retrograde direction, and the D wire inserted in the Luer head. Referring now to FIG. 23, Operator 29 withdraws DAD 56 approximately one centimeter in the retrograde direction indicated by Arrow 63. Through Female Luer Head 61 and "D" Wire Lumen 59, "D" Wire 64 (typically 0.035-inch diameter) is inserted in the direction indicated by Arrow 65 for a few centimeters with J-Tip 67 of "D" Wire 64 exiting Oval Orifice 60, stopping most of the bleed-back. Operator 29 then proceeds either to optional step 17 or to step 18.

FIGS. 32A, 32B, and 32C show the bump configuration at the oval orifice that serves to cause the treatment wire to travel in an axial direction down the vessel when the tip end of the dual-lumen access director is deflected when exiting the SFA. Referring now to FIGS. 32A, 32B, and 32C, DAD 56 has a unique functional characteristic of entering and then purposely exiting a vessel lumen, such as SFA 8. When this occurs, Tip Segment 78 and Taper Segment 80 are designed to deflect in an angle away from the longitudinal axis of the vessel lumen of SFA 8 as the Tip Segment 78 and Taper Segment 80 follow the air-to-air "A" Wire 51 and exit the SFA 8. Because Tip Segment 78 and Taper Segment 80 in a rest position would tend to also deflect the "D" Wire 64 along an angled direction towards the vessel wall of SFA 8 rather than down the vessel lumen of SFA 8, a Bump 81 structure is located at the leading edge of Oval Orifice 60. This configuration of Bump 81 located at the leading edge of Oval Orifice 60 produces—when Tip Segment 78 and Taper Segment 80 deflect and exit the vessel lumen of SFA 8—a "yawning" deformity of Oval Orifice 60.

As shown in FIG. 32A, Tip Segment 78 and Taper Segment 80 are shown in a non-angulation, or rest position, with respect to Larger Diameter Segment 79. If J-Tip 67 of "D" Wire 64 is forced out of Oval Orifice 60 in this position, it is deflected by Bump 81 in Orifice 60 in a direction away from Tip Segment 78 and Taper Segment 80 and into the direction of the vessel wall of SFA 8 (SFA 8 is not shown in FIG. 32A, 32B, or 32C) or possibly into a channel branching off of SFA 8, such as PFA 7.

As shown in FIG. 32B, in transition from the rest position to a function position, as Tip Segment 78 and Taper Segment 80 begin to follow "A" Wire 51 and begin to have a moderate angulation position with respect to Larger Diameter Segment 79, Oval Orifice 60 is stretched and elongated into a "yawning" deformation. This "yawning" deformation of Oval Orifice 60 thins the effective diameter of DAD 56 at the junction of Larger Diameter Segment 79 and Taper Segment 80 and can been seen as a slight Dip 82 on the top surface.

As shown in FIG. 32C, as Tip Segment 78 and Taper Segment 80 further follow "A" Wire 51 and begin to have a severe angulation, or function position, with respect to Larger Diameter Segment 79, Oval Orifice 60 is further stretched and elongated into an enhanced "yawning" deformation, causing further thinning of the effective diameter of DAD 56 at the junction of Larger Diameter Segment 79 and Taper Segment 80 and Dip 82. This thinning allows the Larger Diameter Segment 79 of DAD 56 to point distally down the vessel lumen of SFA 8, allowing extension of "D" Wire 64 without being deflected towards the vessel wall of SFA 8. This directs the J-Tip 67 of "D" Wire 64 along the axis of the vessel lumen of SFA 8 rather than towards the vessel wall of SFA 8. Thus, the combination of Bump 81 located at the leading edge of Oval Orifice 60 provides a combined structure for a functional position that facilitates upward bending of Tip Segment 78 and Taper Segment 80 without associated upward bending of the Larger Diameter Segment 79, causing the yawning deformation of Oval Orifice 60 allowing for intraluminal placement of "D" Wire 64 out of Orifice 60 along the axis of the vessel lumen of SFA 8.

Figure 24:
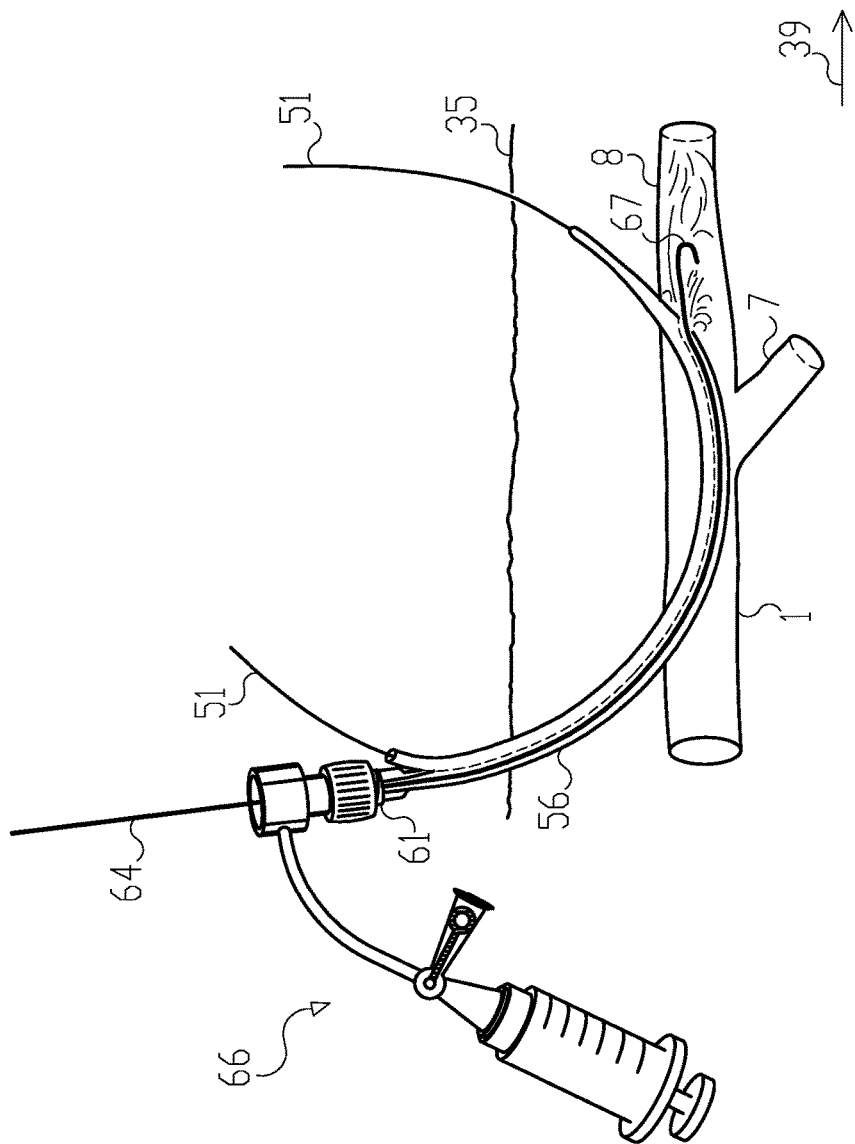
FIG. 24 shows the injection seal and side-port attached to the Luer head.

Step 17. [Optional] FIG. 24 shows the injection seal and side-port attached to the Luer head. Referring now to FIG. 24, Injection Seal And Side-Port 66 is back-loaded over "D" Wire 64 and attached to Female Luer Head 61. Injection Seal And Side-Port 66 is flushed and de-aired by Operator 29. Contrast is injected through the side-port of Injection Seal And Side-Port 66 using either "puff" angiography or a road-mapping technique, both of which are well known by those skilled in the art, and placement of the J-Tip 67 of "D" Wire 64 within the SFA 8 is confirmed. This step is optional as some Operators 29 may have assurance based upon their skill and experience that proper placement has been achieved without this Step 17.

Figure 25:
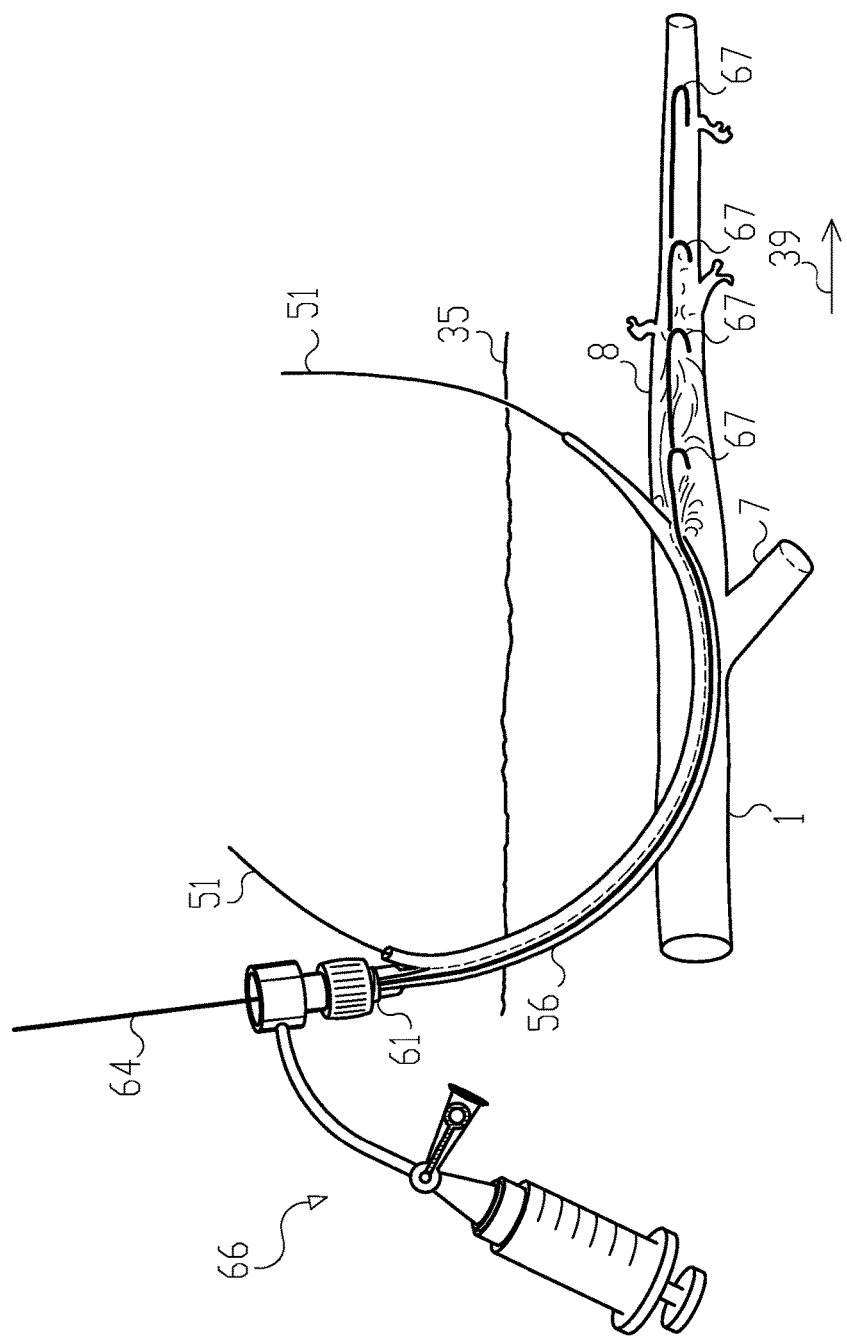
FIG. 25 shows the D wire being passed antegrade down the SFA.

Step 18. FIG. 25 shows the D wire being passed antegrade down the SFA. Referring now to FIG. 25, under either fluoroscopic control or, per optional step 17, angiographic imaging, J-Tip 67 of "D" Wire 64 is passed in the direction indicated by Arrow 39 antegrade down the lumen of SFA 8. J-Tip 67 is shown in four different advancement positions down the lumen of SFA 8 in FIG. 25.

Figure 26:
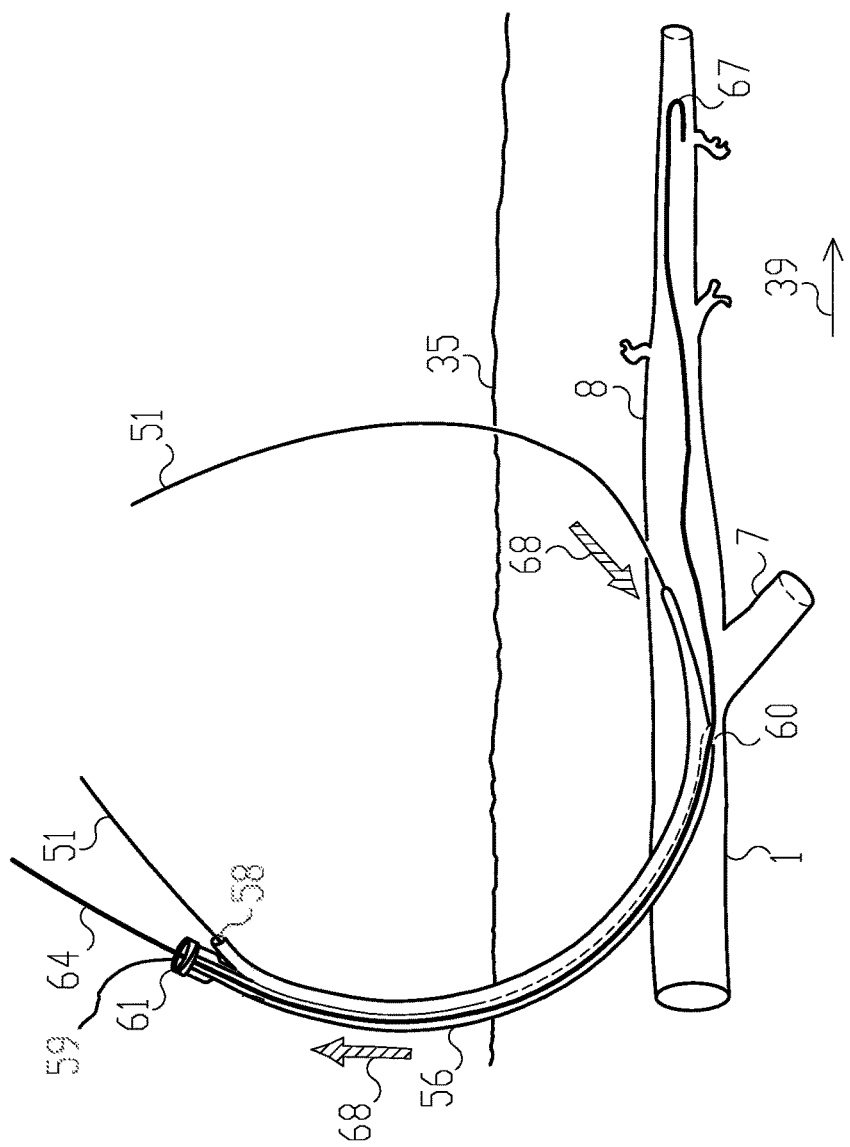
FIG. 26 shows the DAD beginning to be withdrawn.

Step 19. FIG. 26 shows the DAD beginning to be withdrawn. Referring now to FIG. 26, DAD 56 is withdrawn over both "D" Wire 64 and "A" Wire 51 in the direction indicated by Arrows 68.

Figure 27:
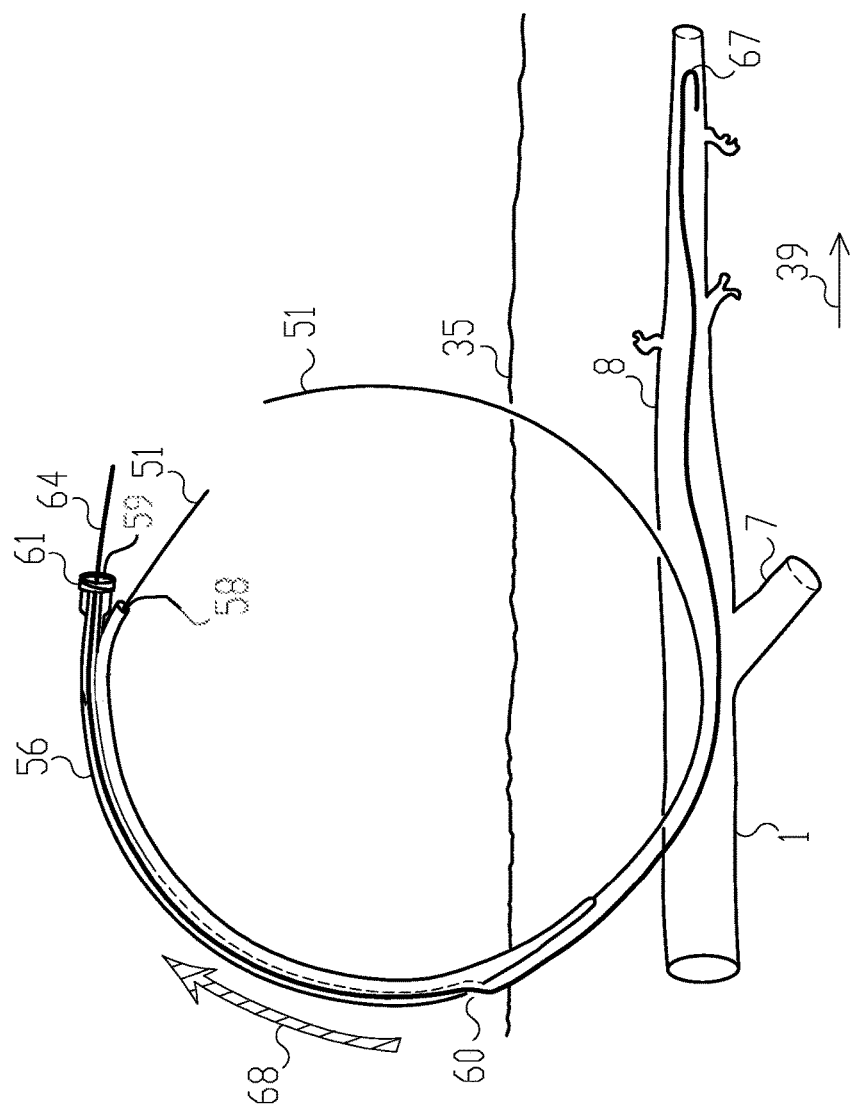
FIG. 27 shows the DAD continuing to be withdrawn.

FIG. 27 shows the DAD continuing to be withdrawn. Referring now to FIG. 27, DAD 56 is completely outside of the CFA 1/SFA 8 lumenal region, leaving only "D" Wire 64 and "A" Wire 51 within the CFA 1/SFA 8 lumenal region.

Figure 28:
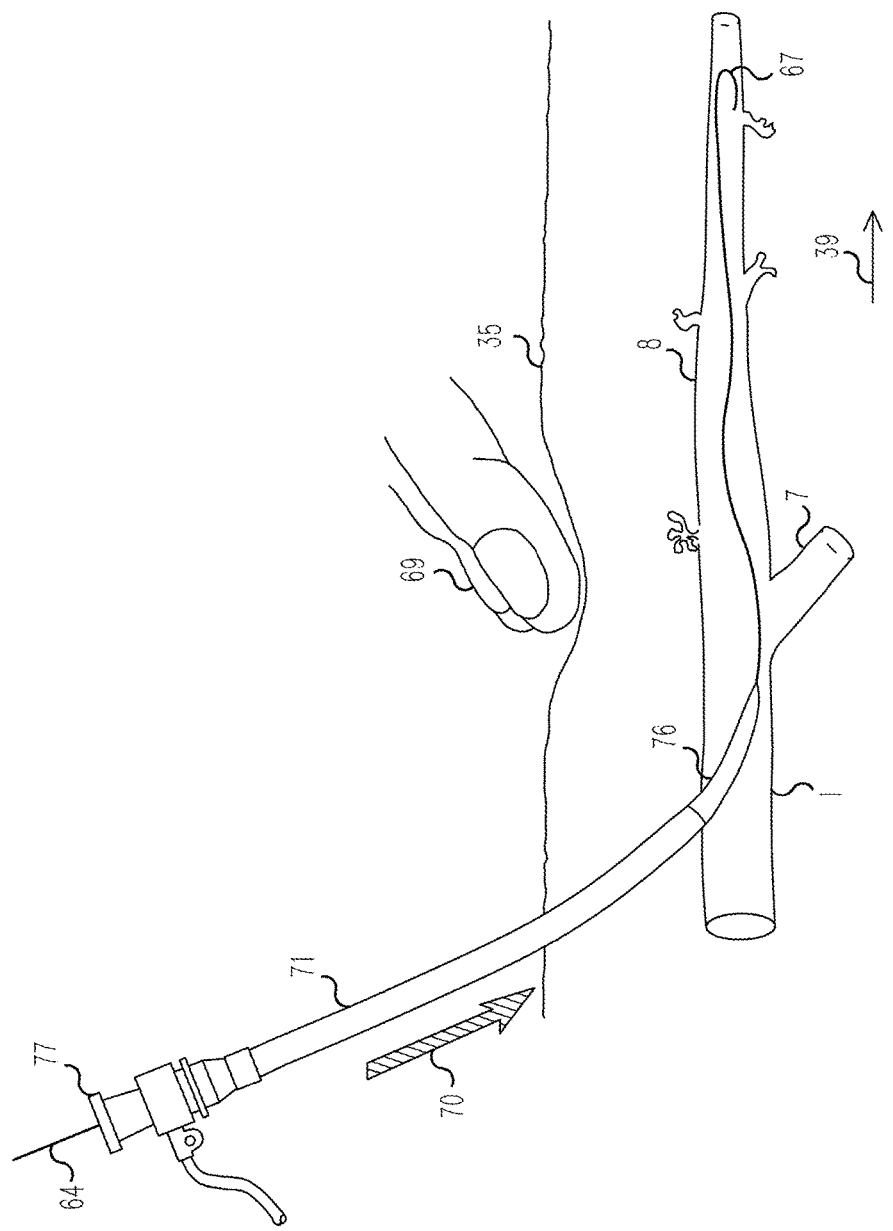
FIG. 28 shows the A wire withdrawn and a standard angiographic sheath and dilator passed over the D wire.

Step 20. FIG. 28 shows the A wire withdrawn and a standard angiographic sheath and dilator passed over the D wire. Referring now to FIG. 28, "A" Wire 51 is withdrawn by pulling either end, and brief pressure is held over the SFA 8 entry-arteriotomy by Fingers 69 of Operator 29 or an assistant. Operator 29 then passes in the direction indicated by Arrow 70 a standard Angiographic Sheath 71 of chosen size and Dilator 76 over "D" Wire 64 into the CFA 1/SFA 8 lumenal region and then in the antegrade direction indicated by Arrow 39. Operator 29 then grasps Dilator Hub 77 and removes Dilator 76 from Angiographic Sheath 71 (shown removed in FIG. 29).

Figure 29:
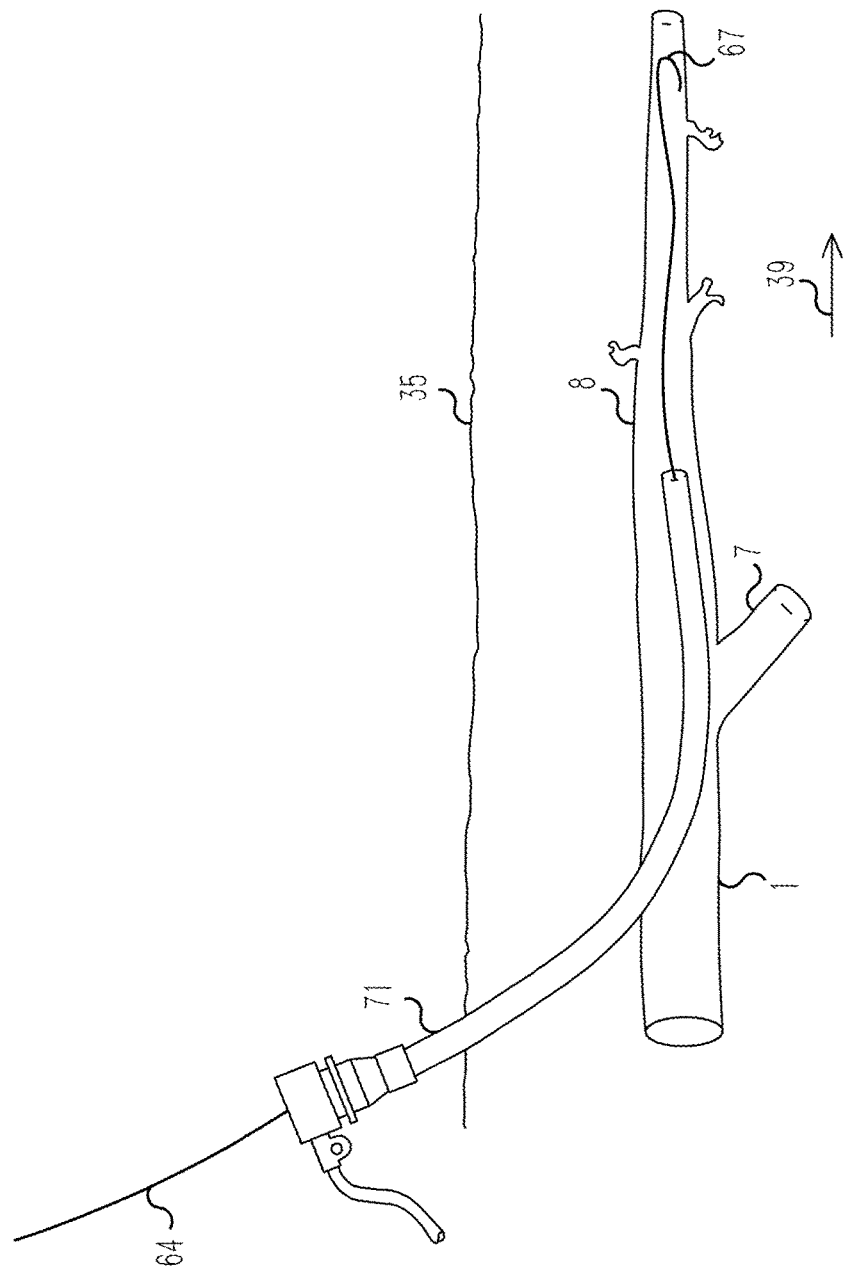
FIG. 29 shows the intended percutaneous procedure being performed in the antegrade direction.

Step 21. FIG. 29 shows the intended percutaneous procedure being performed in the antegrade direction. Referring now to FIG. 29, the intended percutaneous endovascular procedure is now performed by Operator 29 via Angiographic Sheath 71 with Operator 29 working from the left side of Patient 30 in the antegrade direction (see FIG. 18A).

Although the description above has been focused on the CFA 1/SFA 8 vascular area, one skilled in the art will recognize that other applications of the method and devices described above can be applicable to other portions of the body where ease of entry in the vascular system in one direction, and then reversal in the other direction, would be advantageous. Thus, the methodology described above is not limited to the CFA 1/SFA 8 vascular region. In addition, although the description above has been focused on human patients, one skilled in the art will recognize that applications of the method and devices described above can be applicable to mammals or any other organism having a vascular system. Thus, the methodology described above is not limited to humans only.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims. It will be understood by those skilled in the art that many changes in construction and widely differing embodiments and applications will suggest themselves without departing from the scope of the disclosed subject matter.

What is claimed is:

1. An apparatus for aiding vascular access comprising:
   an access director having a first lumen and a second lumen;
   the first lumen extending from a head of the access director to a tip of the access director, the first lumen sized to receive an air-to-air wire to diminish bleed-back, wherein the air-to-air wire extends from outside a skin of a subject and into and out of a vascular channel of the subject and out of the skin of the subject, and wherein the first lumen does not communicate with the vascular channel; and
   the second lumen extending from the head of the access director to a point proximal to the tip that ends in an oval orifice, the oval orifice having a bump located at a leading edge of the oval orifice, wherein the second lumen communicates with the vascular channel and allows bleed-back when the oval orifice is within the vascular channel, the second lumen sized to receive a wire to diminish bleed-back when the wire is received in the second lumen, wherein when the oval orifice is within the vascular channel the wire is deflected by the bump and extended out of the oval orifice and into the vascular channel.

2. The apparatus according to claim 1 further comprising:
   a female Luer head located at the head of the access director, wherein the female Luer head attachably receives one or more devices for aiding vascular access.

3. The apparatus according to claim 2 wherein a one of the one or more devices is an injection seal and side port that is back-loaded over the wire and attached to the female Luer head.

4. The apparatus according to claim 3 wherein the wire has a J-tip.

5. The apparatus according to claim 4 further comprising:
   a contrast injected into the injection seal and side port using a one of a "puff" angiography and a road-mapping technique to confirm placement of the J-tip within the vascular channel.

6. The apparatus according to claim 1 wherein the access director does not have a natural curvature of its own but is flexible and will conform to a curvature of the air-to-air wire.

7. The apparatus according to claim 1 wherein the access director further comprises:
   a larger diameter segment having a first diameter;
   a tip segment having a second diameter that is smaller than the first diameter; and
   a taper segment located between the larger diameter segment and the tip segment having a transitioning diameter that transitions between the first diameter and the second diameter.

8. The apparatus according to claim 7 wherein the first diameter of the larger diameter segment encompasses the first lumen and the second lumen, the transitioning diameter of the taper segment encompasses the second lumen, and the third diameter of the tip segment encompasses the second lumen, wherein the taper segment and the tip segment provide a smooth atraumatic profile that minimizes damage to the vascular channel and the tissue of the subject.

9. The apparatus according to claim 7 wherein the first lumen and the air-to-air wire tether the access director in place to allow extension of the wire out of the oval orifice and into the vascular channel.

10. The apparatus according to claim 9 further comprising:
    a yawning deformation of the oval orifice caused by the bump when the taper segment and the tip segment follow the air-to-air wire and deflect in an angle away from the larger diameter segment, allowing the wire to be extended out of the oval orifice down the vascular channel.

11. The apparatus according to claim 1 wherein the wire has hydrophilic properties.

12. The apparatus according to claim 1 further comprising:
    a dilator; and
    an angiographic sheath;
    wherein the access director is withdrawn over both the air-to-air wire and the wire, the air-to-air wire is withdrawn from the vascular channel and the skin of the subject, the dilator and the angiographic sheath are advanced over the wire and into the vascular channel, and the dilator is removed leaving a tip of the angiographic sheath within the vascular channel for performing an intended percutaneous endovascular procedure.

13. The apparatus according to claim 1 wherein the first lumen and the second lumen are not passage channels for a one or more treatment device.

14. An apparatus for aiding vascular access comprising:
    an access director having a flexible body that does not have a natural curvature of its own, the flexible body further comprising;
    a larger diameter segment having a first diameter;
    a tip segment having a second diameter that is smaller than the first diameter;

a taper segment located between the larger diameter segment and the tip segment having a transitioning diameter that transitions between the first diameter and the second diameter;

an oval orifice located between the larger diameter segment and the taper segment;

a bump located at a leading edge of the oval orifice;

a first lumen extending from a head of the access director and through the larger diameter segment, through the taper segment, and through the tip segment to a tip end of the tip segment, the lumen receives an air-to-air wire that extends from outside a skin of a subject and into and out of a vascular channel of the subject and out of the skin of the subject, wherein the air-to-air wire and the first lumen tether the access director in place; and a second lumen extending from the head of the access director through the larger diameter segment to the oval orifice, the second lumen receives a wire that is extended from the oval orifice and deflected by the bump to direct the wire in a direction down the vascular channel when the oval orifice is tethered within the vascular channel.

15. The apparatus according to claim 14 wherein the first diameter of the larger diameter segment encompasses the first lumen and the second lumen, the transitioning diameter of the taper segment encompasses the second lumen, and the third diameter of the tip segment encompasses the second lumen, wherein the taper segment and the tip segment provide a smooth atraumatic profile that minimizes damage to the vascular channel and the tissue of the subject.

16. The apparatus according to claim 15 wherein the larger diameter segment, after following the air-to-air wire and entering through the skin of the subject and into the vascular channel, is not further advanced to follow the air-to-air wire out of the vascular channel.

17. The apparatus according to claim 14 further comprising:

a rest position of the tip segment and the taper segment with respect to the larger diameter segment, wherein when the wire is extended from the larger diameter segment, the wire is deflected by the bump in the leading edge of the oval orifice in a direction towards a wall of the vascular channel or into a channel branching off of the vascular channel.

18. The apparatus according to claim 17 further comprising:

a function position of the tip segment and the taper segment with respect to the larger diameter segment; and a yawning deformation of the oval orifice caused by the bump due to the function position of the tip segment and the taper segment with respect to the larger diameter segment, wherein when the wire is extended from the larger diameter segment and out of the oval orifice, the wire is not deflected by the bump and extends down the vascular channel.

19. The apparatus according to claim 14 wherein the first lumen and the second lumen are not passage channels for a one or more treatment device.

20. The apparatus according to claim 14 further comprising:

a dilator; and an angiographic sheath;

wherein the access director is withdrawn over both the air-to-air wire and the wire, the air-to-air wire is withdrawn from the vascular channel and the skin of the subject, the dilator and the angiographic sheath are advanced over the wire and into the vascular channel, and the dilator is removed leaving a tip of the angiographic sheath within the vascular channel for performing an intended percutaneous endovascular procedure.

* * * * *